(12) United States Patent
Pfleger et al.

(10) Patent No.: US 8,574,898 B2
(45) Date of Patent: Nov. 5, 2013

(54) TRANSLATION-COUPLING SYSTEMS

(75) Inventors: Brian Pfleger, Madison, WI (US); Daniel Mendez-Perez, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/976,606

(22) Filed: Dec. 22, 2010

(65) Prior Publication Data
US 2012/0021922 A1    Jan. 26, 2012

Related U.S. Application Data

(60) Provisional application No. 61/289,739, filed on Dec. 23, 2009.

(51) Int. Cl.
*C12N 15/00*    (2006.01)

(52) U.S. Cl.
USPC .................. 435/320.1; 536/23.1; 536/24.1

(58) Field of Classification Search
USPC ................................................. 435/320.1
See application file for complete search history.

(56) References Cited

U.S. PATENT DOCUMENTS 5,077,214 A    12/1991 Guarino et al.
5,179,017 A    1/1993 Axel et al.

OTHER PUBLICATIONS

Pfleger et al.; Combinatorial engineering of intergenic regions in operons tunes expression of multiple genes; Nature Biotechnology; vol. 24, No. 8; pp. 1027-1032; published online Jul. 16, 2006; and supplementary material pp. 1-8.*
Geerlof; Ligase Independent Cloning; pp. 1-14; published Jun. 26, 2006.*
Seleem et al.; Enhanced expression, detection and purification of recombinant proteins using RNA stem loop and tandem fusion tags; Applied Microbiology Biotechnology; vol. 75, pp. 1385-1392; published online Jun. 12, 2007.*
Schweizer; Bacterial genetics: past achievements, present state of the field, and future challenges; BioTechniques 44:633-641; published Apr. 2008.*
Mendez-Perez et al.; A translation coupling DNA cassette for monitoring protein translation in *Escherichia coli*; Metabolic Engineering; vol. 14, pp. 298-305; published online May 3, 2012.*
Alper et al., 2005, Tuning genetic control through promoter engineering, *PNAS*, 102(36):12678-83.
Benoist et al., 1981, In vivo sequence requirements of the SV40 early promoter region, *Nature* (London), 290:304.
Bitter et al., 1987, Expression and Secretion Vectors for Yeast, *Methods in Enzymology*, 153:516-544.
Cabrita et al., 2006, A family of *E. coli* expression vectors for laboratory scale and high throughput soluble protein production, *BMC Biotechnology*, 6:12.
Chang et al., 1979, High Frequency Transformation for *Bacillus subtilis* Protoplasts, *Molecular General Genetics*, 168:111-115.
Clark, D.P., 2005, *Molecular Biology*, Academic Press, ISBN 0121755517.
Dubnau et al., 1971, Fate of Transforming DNA following uptake by Competent *Bacillus subtilis*, Journal *of Molecular Biology*, 56:209-221.
Durand et al., 2006, Activation of RegB endoribonucleases by S1 ribosomal protein requires an 11 nt conserved sequence, *Nucleic Acids Research*, 34(22):6549-6560.
Foecking et al., 1980, Powerful and versatile enhancer-promoter unit for mammalian expression vectors, *Gene*, 45:101.
Glick, B., 1987, Factors affecting the expression of foreign proteins in *Escherichia coli, J. Ind. Microbiol.*, 1:277.
Hamer et al., 1982, Regulation In vivo of a Cloned Mammalian Gene: Cadmium Induces the Transcription of a Mouse Metallothionein Gene in SV40 Vectors, *J. Mol. Appl. Gen.*, 1:273.
Hook-Barnard et al., 2007, Identification of an AU-rich Translational Enhancer within the *Escherichia coli fepB* Leader RNA, *J. Bacteriol.*, 189(11):4028-4037.
Johnston et al., 1982, Isolation of the yeast regulatory gene *GAL4* and analysis of its dosage effects on the galactose/melibiose regulon, *PNAS* (USA) 79:6971.
Koehler et al., 1987, *Bacillus subtilis* (*natto*) Plasmid pLS20 Mediates Interspecies Plasmid Transfer, *Journal of Bacteriology*, 169:5271-5278.
McKnight, 1982, Functional Relationships between Transcriptional Control Signals of the Tynidine Kinase Gene of Herpes Simplex Virus, *Cell*, 31:355.
Meinkoth et al., 1986, New RNA Species Is Produced by Alternate Polyadenylation Following Rearrangement Associated with CAD Gene Amplification, *Somat. Cell Mol. Genet.*, 12:339.

(Continued)

*Primary Examiner* — Michele K Joike
*Assistant Examiner* — Antonio Galisteo Gonzalez
(74) *Attorney, Agent, or Firm* — Joseph T. Leone, Esq.; Daniel A. Blasiole; DeWitt, Ross & Stevens, S.C.

(57) ABSTRACT

Disclosed are systems and methods for coupling translation of a target gene to a detectable response gene. A version of the invention includes a translation-coupling cassette. The translation-coupling cassette includes a target gene, a response gene, a response-gene translation control element, and a secondary structure-forming sequence that reversibly forms a secondary structure masking the response-gene translation control element. Masking of the response-gene translation control element inhibits translation of the response gene. Full translation of the target gene results in unfolding of the secondary structure and consequent translation of the response gene. Translation of the target gene is determined by detecting presence of the response-gene protein product. The invention further includes RNA transcripts of the translation-coupling cassettes, vectors comprising the translation-coupling cassettes, hosts comprising the translation-coupling cassettes, methods of using the translation-coupling cassettes, and gene products produced with the translation-coupling cassettes.

21 Claims, 17 Drawing Sheets

(56) References Cited

OTHER PUBLICATIONS

Orlandi et al., 1989, Cloning immunoglobulin variable domains for expression by the polymerase chain reaction *PNAS* (USA) 86:3833.

Salis et al., 2009, Automated design of synthetic ribosome binding sites to control protein expression, *Nature Biotechnology*, 27:946-950.

Sambrook et al., 2001, In: *Molecular Cloning: A Laboratory Manual*, 3$^{rd}$ ed., Cold Spring Harbor Laboratory Press, New York, NY, ISBN-13: 978-0879695774.

Shetty et al., 2008, Engineering BioBrick vectors from BioBrick Parts, *J. Biol. Eng.* Apr. 14;2:5.

Shigekawa et al., 1988, Electroporation of Eukaryotes and Prokaryotes: A General Approach to the Introduction of Macromolecules into Cells, *Biotechniques*, 6:742-751.

Shultzaberger et al., 2001, *Journal of Molecular Biology*, 313(1):215-228.

Silver et al., 1984, Anatomy of *Escherichia coli* Ribosome Binding Sites, *PNAS* (USA) 81:5951.

Watson et al., 1987, Amino terminus of the yeast *GAL4* gene product is sufficient for nuclear localization, *Molecular Biology of The Gene*, 4$^{th}$ Ed., Benjamin Cummins.

Young et al., 1961, Physiological and Genetic Factors Affecting Transformation of *Bacillus subtilis*, *Journal of Bacteriology*, 81:823-829.

* cited by examiner

Bases 10-51 of SEQ ID NO:1 (TC1)

Bases 19-64 of SEQ ID NO:2 (TC2)

Bases 19-64 of SEQ ID NO:4 (TC4)

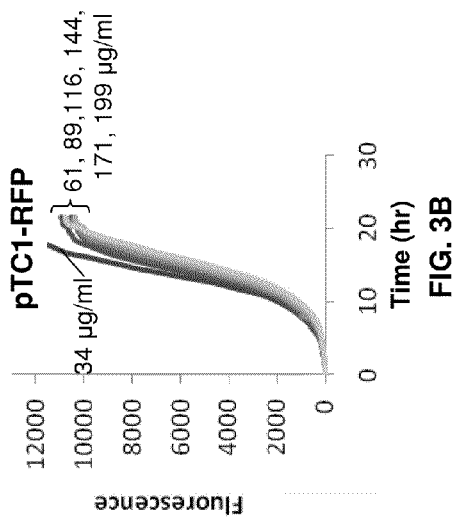
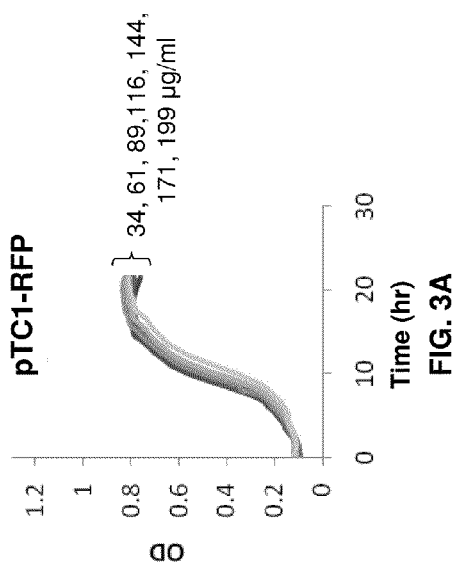
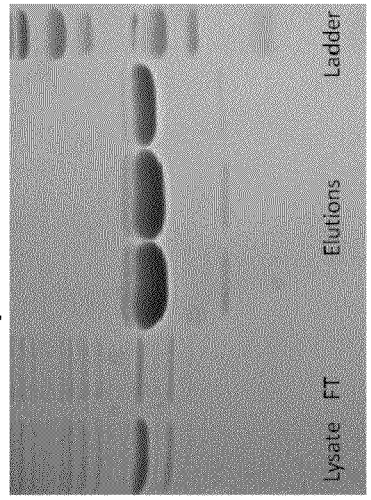
FIG. 3A
FIG. 3B
FIG. 3C

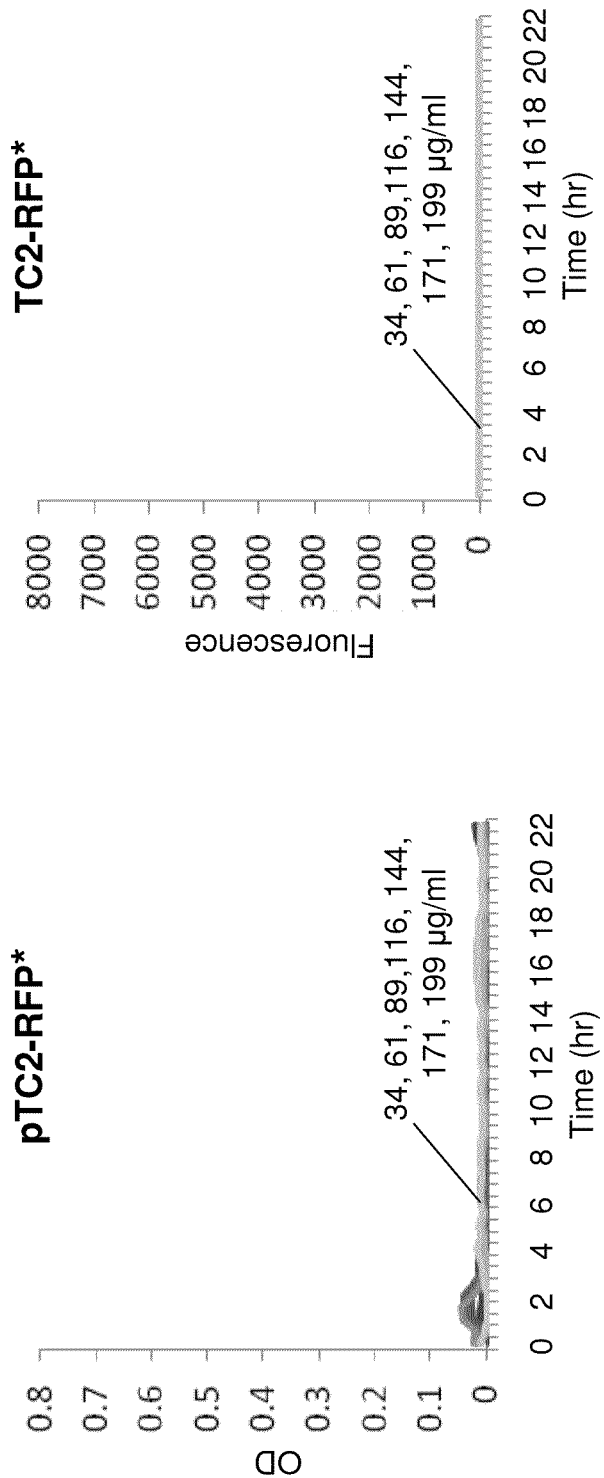

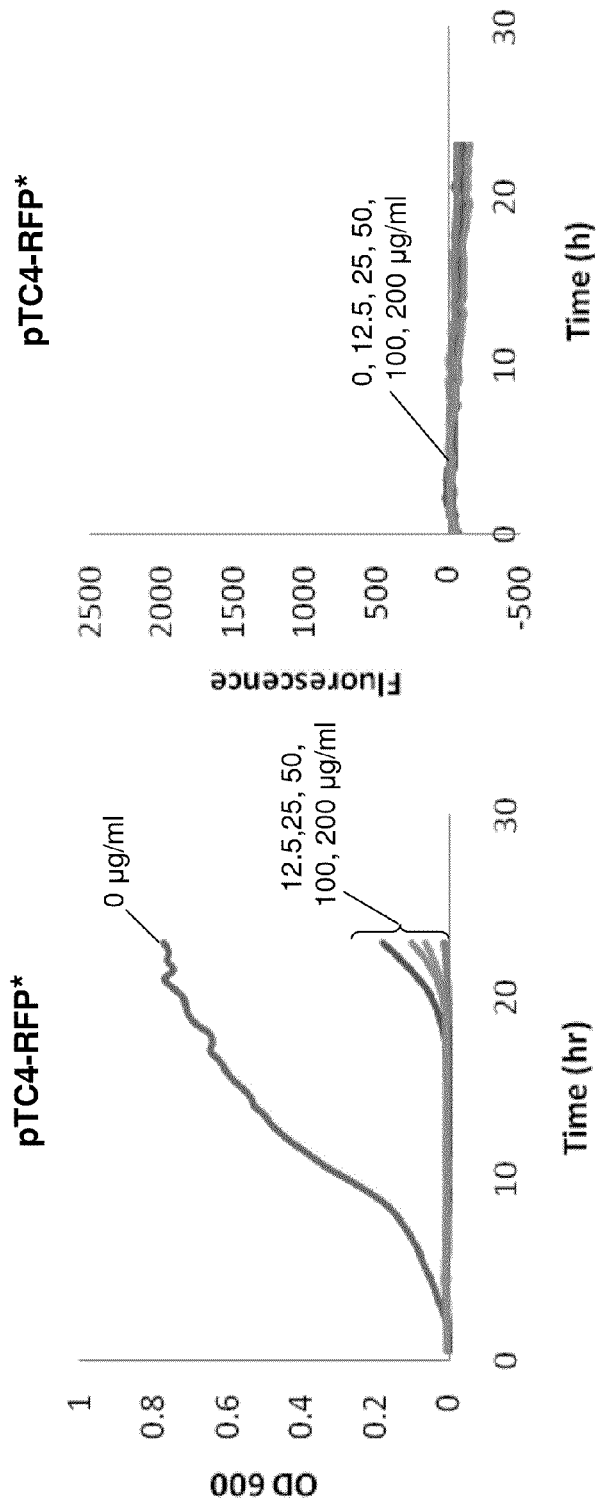

SEQUENCE LISTING

```
<160> NUMBER OF SEQ ID NOS: 5

<210> SEQ ID NO 1
<211> LENGTH: 708
<212> TYPE: DNA
<213> ORGANISM: Artificial Sequence
<220> FEATURE:
<223> OTHER INFORMATION: TC1 translation coupling cassette
<220> FEATURE:
<221> NAME/KEY: stem_loop
<222> LOCATION: (18)..(46)
<220> FEATURE:
<221> NAME/KEY: RBS
<222> LOCATION: (35)..(40)

<400> SEQUENCE: 1
gaattcaaaa gatctcatca tcaccaccac cattaggagg tgatgaaaat ggagaaaaaa      60
atcactggat ataccaccgt tgatatatcc caatggcatc gtaaagaaca ttttgaggca     120
tttcagtcag ttgctcaatg tacctataac cagaccgttc agctggatat tacggccttt    180
ttaaagaccg taaagaaaaa taagcacaag ttttatccgg cctttattca cattcttgcc    240
cgcctgatga atgctcatcc ggagttccgt atggcaatga aagacggtga gctggtgata    300
tgggatagtg ttcacccttg ttacaccgtt ttccatgagc aaactgaaac gttttcatcg    360
ctctggagtg aataccacga cgatttccgg cagtttctac acatatattc gcaagatgtg    420
gcgtgttacg gtgaaaacct ggcctatttc cctaaagggt ttattgagaa tatgttttc     480 gtcagcgcca atccctgggt gagtttcacc agttttgatt taaacgtggc caatatggac    540
aacttcttcg cccccgtttt cactatgggc aaatattata cgcaaggcga caggtgctg    600 atgccgctgg cgattcaggt tcatcatgcc gtctgtgatg gcttccatgt cggcagaatg    660
cttaatgaat tacaacagta ctgcgatgag tggcagggcg ggcgtaa                   708

<210> SEQ ID NO 2
<211> LENGTH: 721
<212> TYPE: DNA
<213> ORGANISM: Artificial Sequence
<220> FEATURE:
<223> OTHER INFORMATION: TC2 translation coupling cassette
<220> FEATURE:
<221> NAME/KEY: stem_loop
<222> LOCATION: (26)..(60)
<220> FEATURE:
<221> NAME/KEY: RBS
<222> LOCATION: (48)..(53)

<400> SEQUENCE: 2
agatctaaat aggaggaaga attccatcat caccaccatc attaggatgg tggtgatgat      60
aatggagaaa aaaatcactg gatataccac cgttgatata tcccaatggc atcgtaaaga    120
acattttgag gcatttcagt cagttgctca atgtacctat aaccagaccg ttcagctgga    180
tattacggcc tttttaaaga ccgtaaagaa aaataagcac aagtttatc cggcctttat     240
```

| | | |
|---|---|---|
| tcacattctt gcccgcctga tgaatgctca tccggagttc cgtatggcaa tgaaagacgg | 300 | |
| tgagctggtg atatgggata gtgttcaccc ttgttacacc gttttccatg agcaaactga | 360 | |
| aacgttttca tcgctctgga gtgaatacca cgacgatttc cggcagtttc tacacatata | 420 | |
| ttcgcaagat gtggcgtgtt acggtgaaaa cctggcctat ttccctaaag ggtttattga | 480 | |
| gaatatgttt ttcgtcagcg ccaatccctg ggtgagtttc accagttttg atttaaacgt | 540 | |
| ggccaatatg gacaacttct tcgcccccgt tttcactatg ggcaaatatt atacgcaagg | 600 | |
| cgacaaggtg ctgatgccgc tggcgattca ggttcatcat gccgtctgtg atggcttcca | 660 | |
| tgtcggcaga atgcttaatg aattacaaca gtactgcgat gagtggcagg gcggggcgta | 720 | |
| a | 721 | |

<210> SEQ ID NO 3
<211> LENGTH: 721
<212> TYPE: DNA
<213> ORGANISM: Artificial Sequence
<220> FEATURE:
<223> OTHER INFORMATION: TC3 translation coupling cassette
<220> FEATURE:
<221> NAME/KEY: stem_loop
<222> LOCATION: (26)..(60)
<220> FEATURE:
<221> NAME/KEY: RBS
<222> LOCATION: (48)..(53)

<400> SEQUENCE: 3

| | | |
|---|---|---|
| caattgaaat aggaggaaac tagtcatcat caccaccatc attaggatgg tggtgatgat | 60 | |
| aatggagaaa aaaatcactg gatataccac cgttgatata tcccaatggc atcgtaaaga | 120 | |
| acattttgag gcatttcagt cagttgctca atgtacctat aaccagaccg ttcagctgga | 180 | |
| tattacggcc ttttttaaaga ccgtaaagaa aaataagcac aagttttatc cggcctttat | 240 | |
| tcacattctt gcccgcctga tgaatgctca tccggagttc cgtatggcaa tgaaagacgg | 300 | |
| tgagctggtg atatgggata gtgttcaccc ttgttacacc gttttccatg agcaaactga | 360 | |
| aacgttttca tcgctctgga gtgaatacca cgacgatttc cggcagtttc tacacatata | 420 | |
| ttcgcaagat gtggcgtgtt acggtgaaaa cctggcctat ttccctaaag ggtttattga | 480 | |
| gaatatgttt ttcgtcagcg ccaatccctg ggtgagtttc accagttttg atttaaacgt | 540 | |
| ggccaatatg gacaacttct tcgcccccgt tttcactatg ggcaaatatt atacgcaagg | 600 | |
| cgacaaggtg ctgatgccgc tggcgattca ggttcatcat gccgtctgtg atggcttcca | 660 | |
| tgtcggcaga atgcttaatg aattacaaca gtactgcgat gagtggcagg gcggggcgta | 720 | |
| a | 721 | |

<210> SEQ ID NO 4
<211> LENGTH: 871
<212> TYPE: DNA
<213> ORGANISM: Artificial Sequence
<220> FEATURE:
<223> OTHER INFORMATION: TC4 translation coupling cassette
<220> FEATURE:
<221> NAME/KEY: stem_loop
<222> LOCATION: (26)..(60)
<220> FEATURE:
<221> NAME/KEY: RBS
<222> LOCATION: (48)..(53)

<400> SEQUENCE: 4

| | | |
|---|---|---|
| caattgaaat aggaggaaac tagtcatcat caccaccatc attaggatgg tggtgatgat | 60 | |
| aatgagccat attcaacggg aaacgtcgag gccgcgatta aattccaaca tggatgctga | 120 | |

```
tttatatggg tataaatggg ctcgcgataa tgtcgggcaa tcaggtgcga caatctatcg      180
cttgtatggg aagcccgatg cgccagagtt gtttctgaaa catggcaaag gtagcgttgc      240
caatgatgtt acagatgaga tggtcagact aaactggctg acggaattta tgccacttcc      300
gaccatcaag cattttatcc gtactcctga tgatgcatgg ttactcacca ctgcgatccc      360
cggaaaaaca gcgttccagg tattagaaga atatcctgat tcaggtgaaa atattgttga      420
tgcgctggca gtgttcctgc gccggttgca ctcgattcct gtttgtaatt gtccttttaa      480
cagcgatcgc gtatttcgcc tcgctcaggc gcaatcacga atgaataacg gtttggttga      540
tgcgagtgat tttgatgacg agcgtaatgg ctggcctgtt gaacaagtct ggaaagaaat      600
gcataaactt ttgccattct caccggattc agtcgtcact catggtgatt tctcacttga      660
taaccttatt tttgacgagg ggaaattaat aggttgtatt gatgttggac gagtcggaat      720
cgcagaccga taccaggatc ttgccatcct atggaactgc ctcggtgagt tttctccttc      780
attacagaaa cggcttttc aaaaatatgg tattgataat cctgatatga ataaattgca      840
gtttcatttg atgctcgatg agtttttcta a                                    871

<210> SEQ ID NO 5
<211> LENGTH: 53
<212> TYPE: DNA
<213> ORGANISM: Artificial Sequence
<220> FEATURE:
<223> OTHER INFORMATION: TC5 translation coupling cassette
<220> FEATURE:
<221> NAME/KEY: stem_loop
<222> LOCATION: (5)..(51)
<220> FEATURE:
<221> NAME/KEY: RBS
<222> LOCATION: (29)..(34)

<400> SEQUENCE: 5
aacactagtc atcatcacca ccatcattag gatggtggtg atgataatga gcc             53
```

TRANSLATION-COUPLING SYSTEMS

CROSS REFERENCE TO RELATED APPLICATIONS

This application claims priority under 35 USC §119(e) to U.S. Provisional Patent Application 61/289,739 filed Dec. 23, 2009, the entirety of which is incorporated herein by reference.

STATEMENT REGARDING FEDERALLY SPONSORED RESEARCH

This invention was made with United States government support awarded by the following agencies: U.S. Department of Energy, DE-FC02-07ER64494. The United States government has certain rights in this invention.

FIELD OF THE INVENTION

The invention is directed to systems and methods for coupling translation of a target gene to a response gene in a host.

BACKGROUND

Production of recombinant proteins in hosts is a common process used both by researchers and commercial entities for the manufacture of a large variety of proteins. In many instances, the protein is not produced efficiently in particular host, so these proteins must be produced through a different expression system. Unfortunately, conventional methods of determining the efficiency of protein expression in a particular host require a number of time-consuming steps. One method involves destroying the host, isolating proteins therefrom, and resolving the isolated proteins on a gel to detect the presence of product bands at a particular molecular weight. Another method involves destroying the host, and performing a Western blot for the protein of interest. In addition to being time-consuming, both methods involve either knowledge of the size of the protein of interest or an antibody that specifically recognizes the expressed product. Further, the researcher does not know about failed expression until all the steps are performed. The ability to monitor protein translation directly in hosts, particularly in real-time, is limited.

One method of monitoring protein expression in real-time in hosts is to fuse the protein of interest directly to a fluorescent protein. Protein translation is measured through detection of fluorescence in the host. However, this method is limited in that fusion of the proteins can affect activity of both the protein of interest and the fluorescent protein and makes purification and isolation of the protein of interest difficult.

Therefore, there remains a long-felt and unmet need for a system and method for quickly and reliably determining whether any given host is capable of expressing the gene product of any given gene.

SUMMARY OF THE INVENTION

The present invention is directed to systems and methods for coupling translation of any desired target gene to a response gene in a host. If the target gene is successfully translated, the response gene is likewise translated and, preferably, can be detected. If the target gene is not fully translated, the response gene is not translated, and the function of the protein encoded by the response gene cannot be detected. In an exemplary version of the invention, the coupling of translation between the target gene and the response gene occurs by including the response gene downstream of the target gene on the same translation-coupling cassette or vector. A response-gene translation control element, such as a ribosome binding site, that controls translation of the response gene but not the target gene is included between the target gene and the response gene in a sequence that reversibly adopts a secondary structure when transcribed into RNA. The secondary structure occludes binding of ribosomes to the response-gene translation control element or otherwise blocks its function such that translation of the response gene cannot occur. The sequence adopting the secondary structure, however, is translationally linked to the target gene such that full translation of the target gene unfolds the RNA secondary structure in the RNA transcript, unmasks the response-gene translation control element, and thereby permits translation of the response gene. This system can be used to screen for target-gene mutants that express in a particular host, determine culture conditions that enable a host to efficiently express a target gene, or screen a DNA library for factors that facilitate expression of a target gene.

Accordingly, one version of the invention includes a translation-coupling cassette that comprises either a target gene or a target-gene cloning site, a response gene or a response-gene cloning site, a response-gene translation control element, and a secondary structure-forming sequence that, when transcribed, reversibly forms a secondary structure that masks the response-gene translation control element, wherein at least part of the secondary structure-forming sequence is translationally linked with the target-gene cloning site or the target gene.

The cloning sites can be multiple cloning sites, ligation-independent cloning sites, or any other cloning sites amenable to insertion of a gene therein.

The response gene can be a screenable gene or a selectable gene.

The response-gene translation control element is preferably a ribosome binding site. In some versions, the ribosome binding site comprises a Shine-Dalgarno sequence or derivative thereof. In other versions, the ribosome binding site comprises an AT-rich sequence. The translation-coupling cassette may further include a linker disposed between the response-gene translation control element and the response gene or the response-gene cloning site.

The translation-coupling cassette may further include a stop codon upstream, within, or downstream of the secondary structure-forming sequence, the stop codon being translationally linked with the target-gene cloning site or in-frame and translationally linked with the target gene. Including the stop codon within or downstream of the secondary structure-forming sequence is preferred, and including the stop codon within the secondary structure-forming sequence is most preferred.

The translation-coupling cassette can further include a protein tag-encoding sequence, wherein the protein tag-encoding sequence is translationally linked with the target-gene cloning site or in-frame and translationally linked with the target gene.

The secondary structure formed by the transcribed secondary structure-forming sequence preferably includes a stem loop.

In a preferred version, the secondary structure-forming sequence includes at least a portion of a response-gene translation control element; a stop codon, wherein the stop codon is translationally linked with the target-gene cloning site or in-frame and translationally linked with the target gene; and at least a portion of a protein tag-encoding sequence, wherein the protein tag-encoding sequence is translationally linked with the target-gene cloning site or in-frame and translationally linked with the target gene. Exemplary secondary structure-forming sequences include bases 18-46 of SEQ ID NO:1, bases 26-60 of SEQ ID NO:2, bases 26-60 of SEQ ID NO:3, bases 26-60 of SEQ ID NO:4, and bases 5-51 of SEQ ID NO:5.

In some versions of the invention, the translation-coupling cassette is included within a vector capable of being introduced in a host.

In some versions of the invention, the translation-coupling cassette is included within a host, preferably a prokaryotic host.

The invention also includes RNA molecules formed by transcription of any of the versions of the translation-coupling cassette described herein.

The invention also includes methods of assessing expression of a target gene using a translation-coupling cassette as described herein.

One method includes introducing a translation-coupling cassette into a host and determining a level of expression of the response gene.

Another method further includes generating a mutated version of the target gene, cloning the mutated version of the target gene into a translation-coupling cassette, introducing the translation-coupling cassette with the mutated version of the target gene into a host, determining the level of expression of the response gene in the host, and comparing the level of expression with that of non-mutated versions.

Another method includes culturing the host in a plurality of culture conditions, determining a level of response-gene expression for each of the plurality of culture conditions, and comparing the levels of response-gene expression for each of the plurality of culture conditions.

Another method includes introducing into a host a translation-coupling cassette in a first vector and a clone from a DNA library, such as a genomic, cDNA, or metagenomic library in a second vector, to screen for factors that enhance target-gene expression.

Among other advantages, the methods of assessing protein translation described herein are quick and involve few processing tasks. The methods do not impact the activity of the protein of interest or complicate subsequent isolation and purification methods.

The invention also includes gene products fabricated by any of the methods or procedures described herein. One version includes a gene product fabricated by translating a gene from a transcript of a translation-coupling cassette as described herein, wherein the gene is selected from the group consisting of a target gene and a response gene.

The objects and advantages of the invention will appear more fully from the following detailed description of the preferred embodiment of the invention made in conjunction with the accompanying drawings.

BRIEF DESCRIPTION OF THE DRAWINGS

FIGS. 3A, 3B, and 3C show growth curves, fluorescence curves, and an SDS-PAGE analysis of purified target-gene protein product, respectively, from *E. coli* cells transformed with the pTC1-RFP plasmid (see Tables 1 and 2) and grown in the presence of the shown concentrations (μg/ml) of chloramphenicol.

FIGS. 6A and 6B show growth and fluorescence curves, respectively, from *E. coli* cells transformed with the pTC2-RFP* plasmid (see Tables 1 and 2) and grown in the presence of the shown concentrations (μg/ml) of chloramphenicol.

FIGS. 8A and 8B show growth and fluorescence curves, respectively, from *E. coli* cells transformed with the pTC4-

RFP* plasmid (see Tables 1 and 2) and grown in the presence of the shown concentrations (μg/ml) of kanamycin.

Figure 9:
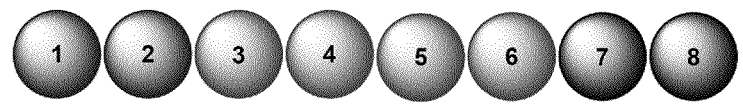

FIG. 9 depicts the predicted domain structure of a previously uncharacterized and unexpressed gene ("Gene X"). Eight predicted domains, Domains 1-8, are shown.

Figure 10:
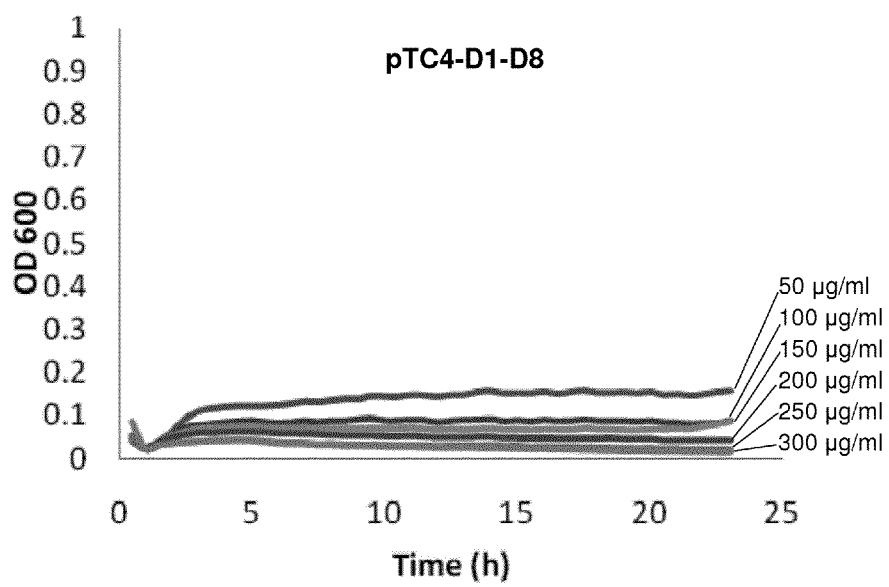

FIG. 10 shows a growth curve from *E. coli* cells transformed with the pTC4-D1-D8 plasmid (see Tables 1 and 2), comprising full-length Gene X and grown in the presence of the shown concentrations (μg/ml) of kanamycin.

Figures 11A, 11B:
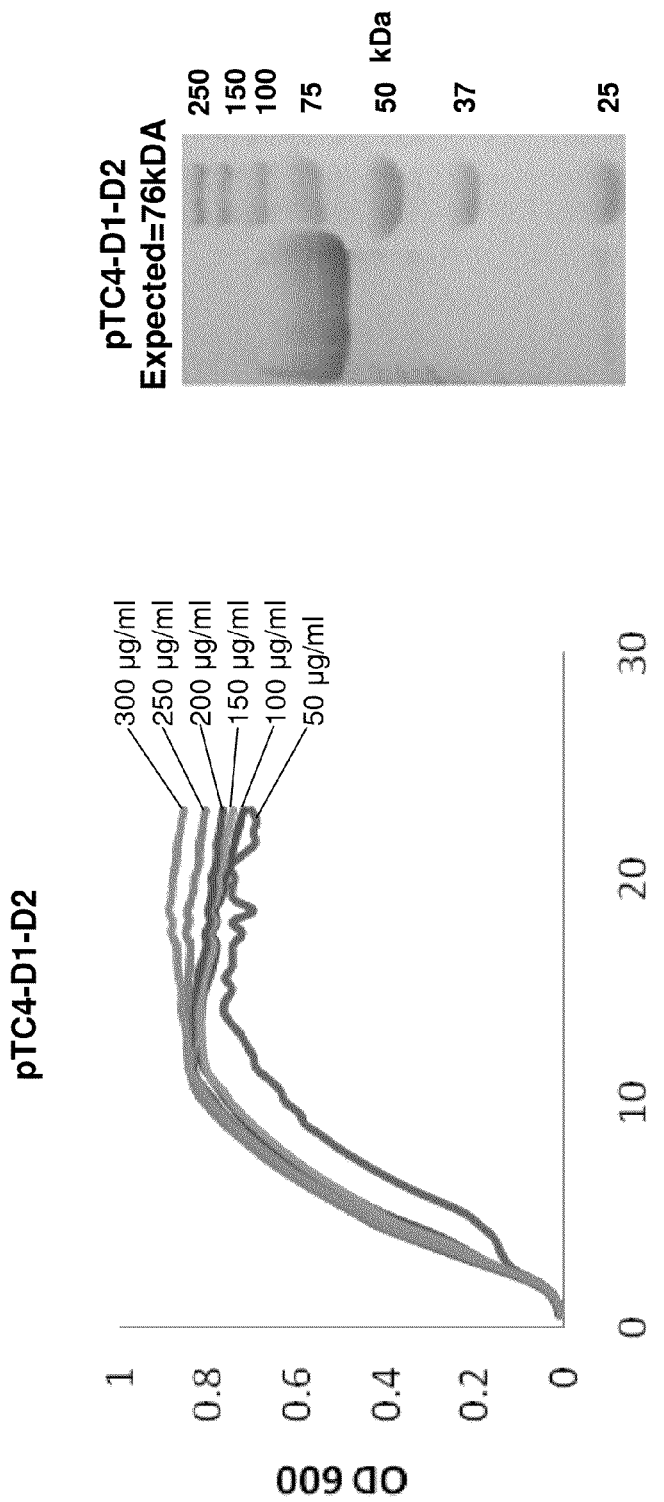

FIGS. 11A and 11B a show a bacterial growth curve and an SDS-PAGE analysis of purified target-gene protein product, respectively, from *E. coli* cells transformed with the pTC4-D1-D2 plasmid (see Tables 1 and 2), comprising only the portion of Gene X encoding Domains 1 and 2, and grown in the presence of the shown concentrations (μg/ml) of kanamycin.

Figures 12A, 12B:
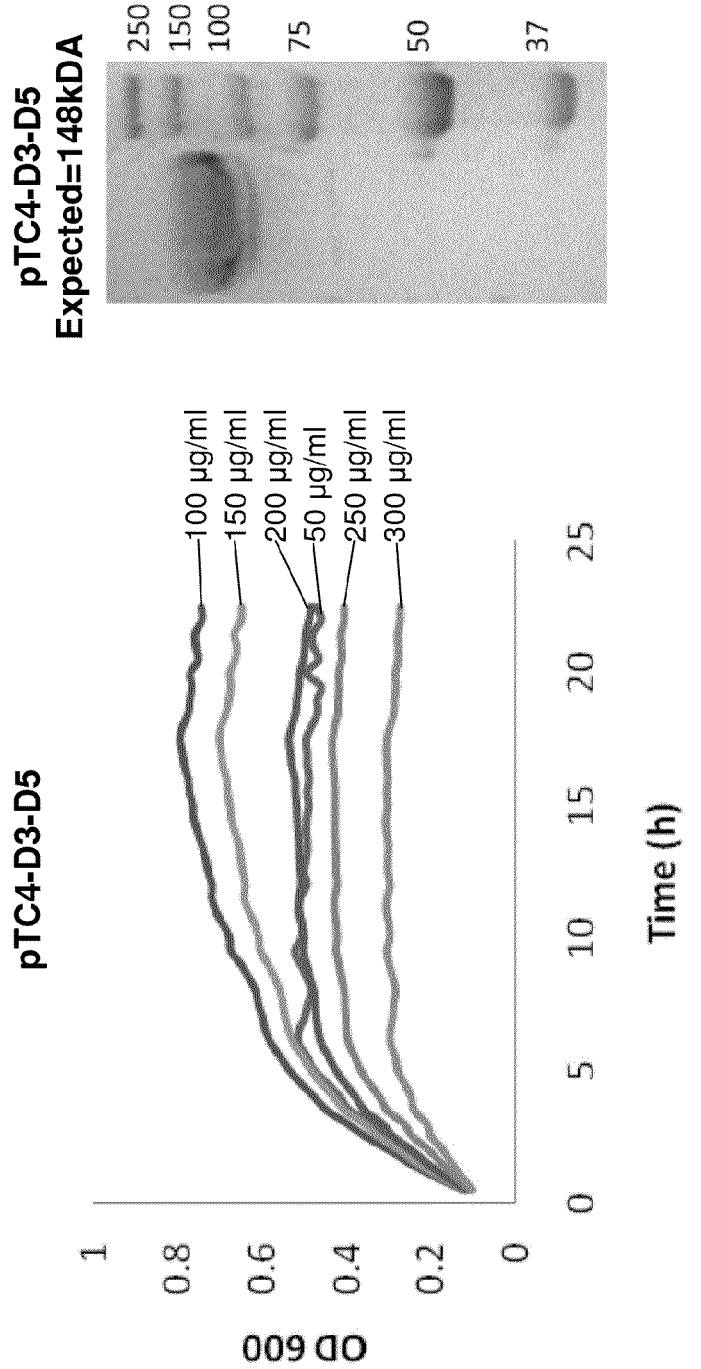

FIGS. 12A and 12B a show a bacterial growth curve and an SDS-PAGE analysis of purified target-gene protein product, respectively, from *E. coli* cells transformed with the pTC4-D3-D5 plasmid (see Tables 1 and 2), comprising only the portion of Gene X encoding Domains 3-5, and grown in the presence of the shown concentrations (μg/ml) of kanamycin.

Figure 13B:
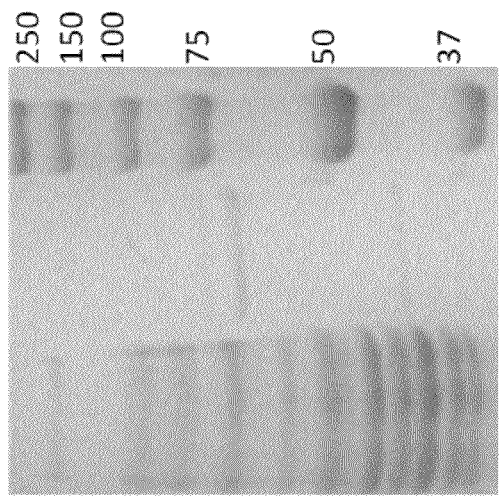
Figure 13A:
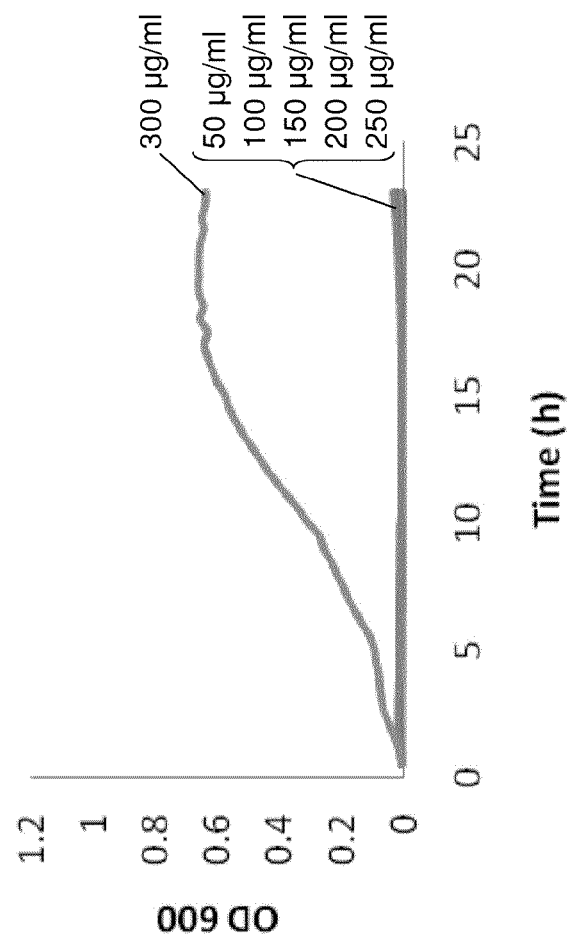

FIGS. 13A and 13B a show a bacterial growth curve and an SDS-PAGE analysis of purified target-gene protein product, respectively, from *E. coli* cells transformed with the pTC4-D6-D8 plasmid (see Tables 1 and 2), comprising only the portion of Gene X encoding Domains 6-8, and grown in the presence of the shown concentrations (μg/ml) of kanamycin.

DETAILED DESCRIPTION OF THE INVENTION

The present invention comprises a translation-coupling cassette that couples full translation of a target gene (and translationally linked sequences, excluding stop codons) to the expression of a selectable, screenable, and/or otherwise detectable response gene. Versions of the translation-coupling cassette accordingly include either a target gene or a target-gene cloning site for insertion of a target gene, together with a response gene or a response-gene cloning site for insertion of a response gene.

Whether used with reference to a target gene or a response gene, "gene" refers to a nucleic acid sequence that includes at least one start codon followed by a coding sequence for at least one polypeptide. For the purposes herein, "gene" may or may not include a stop codon, a promoter, enhancers, or other elements required for its expression (see below). A gene may include introns in addition to exons, particularly if derived from eukaryotic genomic DNA. Genes that include introns are preferably expressed in eukaryotic hosts or other expression systems capable of excising the introns. Genes configured for being expressed in prokaryotic hosts preferably do not include introns. As used herein, references to a "gene," such as a "target gene" or a "response gene," refers to sequences on a DNA translation-coupling cassette and any corresponding sequences on a transcript thereof, unless explicitly stated otherwise or otherwise implied by the context.

"Target gene" refers to any gene encoding a polypeptide that is desired to be expressed for any purpose. The target gene is typically heterologous to a host but may also be native to the host. If the target gene is native to the host, its expression may be desired under conditions different than those under which it is normally expressed, or its expression may be desired at levels greater than or less than those at which it is normally expressed. The target gene can be obtained by any method, including cloning from genomic or cDNA libraries, subcloning from gene fragments, or, if the nucleotide sequence is known, direct synthesis. Techniques for cloning and subcloning DNA and generating genomic DNA and cDNA libraries are widely known to those of skill in the art. DNA synthesis can be performed by any of several commercially available synthesizers known to those skilled in the art. In a preferred version of the invention, the target gene does not include its own promoter and relies on a promoter elsewhere in a vector harboring the translation-coupling cassette to initiate its transcription. It is also preferred that the target gene does not include its own stop codon and instead relies on a stop codon elsewhere in the translation-coupling cassette, such as in a secondary structure-forming sequence (see below), to stop its translation. To facilitate read-through of the ribosome to a stop codon in the translation-coupling cassette, the target gene preferably does not include its own 3' untranslated region (3' UTR). As used herein, "translation of the target gene" refers to translation of the coding sequence of the target gene on an RNA transcript of the translation-coupling cassette.

In place of a target gene, the translation-coupling cassette may include a target-gene cloning site configured for insertion of a target gene. The cloning site may comprise any sequence of nucleic acid residues amenable to insertion, by any method (i.e., ligation, ligation-independent cloning, homologous recombination, ligation, etc.), of a target gene therein. In one version, the cloning site includes one or more restriction sites for digesting with an appropriate restriction enzyme and inserting a desired target gene therein. For example, the cloning site may comprise a multiple cloning site (MCS), also called a polylinker. An MCS is a short segment of DNA containing several (up to 20 or more) different restriction sites. Examples of restriction sites that can comprise an MCS include, without limitation, EcoRI, BglII, ClaI, PvuI, BamHI, KpnI, XbaI, SalI, HindI, PstI, and SpeI. MCSs are a standard feature of many commercially available plasmids. See, for example, Clark D P (2005), "Molecular Biology," Academic Press, ISBN 0121755517, at page 611. Any of these MCSs are suitable for use in the present invention. It is preferable that any restriction site in the cloning site occurs only once within a given translation-coupling cassette or plasmid containing it.

The cloning site may also comprise a ligation-independent cloning site. Design of ligation-independent cloning sites and methods of ligation-independent cloning are well known in the art. See, e.g., Cabrita et al. *BMC Biotechnology* (2006) 6:12. Briefly, the cloning site is designed around restriction sites such that the 16-18 or so bases surrounding the restriction site are missing one of the four nucleotides, such as adenine (A). One example of ligation-independent cloning with such a site is T4 polymerase-mediated ligation-independent cloning (T4P-LIC). The vector comprising the translation-coupling cassette is first linearized by a restriction enzyme or enzymes at the cloning site. The vector is treated with T4 DNA polymerase in the presence of only a single type of nucleotide, such as dATP, for example. The exonuclease activity degrades the exposed 3' ends of the linearized vector until reaching the first A base, at which point the T4 DNA polymerase's exonuclease and polymerase activities balance each other out, leaving the vector with 16-18-base, 5' overhangs. The insert is amplified by PCR using oligos with tails that, when treated with T4 polymerase and dTTP, create overhangs compatible with those on the vector. The vector and insert are then annealed together and transformed. The long sticky ends on the plasmid and insert are sufficient to hold the plasmid and insert together, allowing them to be transformed without prior ligation. The existing nicks are then repaired by ligases in the host cell. If the left and right sticky ends on the plasmid are different, the cloning is directional.

Other cloning sites include BioBrick® cloning sites (Shetty et al. *J. Biol Eng.* (2008) Apr. 14; 2:5).

Non-limiting examples of cloning sites for use in the present invention and the placement of the target-gene cloning site with respect to the other elements in the translation-coupling cassette include bases 1-15 of SEQ ID NO:1, bases 1-24 of SEQ ID NO:2 (ligation-independent cloning competent), bases 1-24 of SEQ ID NO:3, bases 1-24 of SEQ ID NO:4, and bases 1-9 of SEQ ID NO:5. FIGS. 2A-2E show downstream restriction sites of these cloning sites.

Regardless of the type of cloning site used, steps can and should be taken to ensure that any target gene inserted in the cloning site is in-frame with any sub-elements that are translationally linked with the cloning site, such as a protein tag-encoding sequence and a stop codon (see below). This can be done with appropriate cloning strategies, which are well-known in the art.

The target gene or target-gene cloning site is preferably operably linked to a sequence encoding an element responsible for controlling translation of the existing target gene or any subsequently inserted target gene, but not the response gene. As used herein, "controlling translation" refers to any mechanism of inducing translation, including but not limited to promoting initiation of translation. Such an element is preferably a ribosome binding site, examples of which are discussed in further detail below.

"Response gene" also refers to any gene encoding a polypeptide that is desired to be expressed for any purpose. In a preferred version of the invention, the response gene is any gene that encodes a product capable of being detected upon expression. It is preferable that such detection is amenable to high-throughput detection, real-time detection, or automated detection. Successful expression of a response gene confers the ability to distinguish between hosts (and their progeny) that express the response gene and hosts (and their progeny) that do not express the response gene. Examples of genes that are capable of being detected include selectable response genes and screenable response genes. As used herein, "translation of the response gene" refers to translation of the coding sequence of the response gene on an RNA transcript of the translation-coupling cassette.

Selectable response genes are genes that confer the ability to select a host expressing the gene from those that do not express the gene. Selectable response genes typically confer resistance to a selection agent that kills hosts not expressing the gene. Non-limiting examples of selectable response genes include antibiotic resistance genes; auxotrophic complementation genes, herbicide tolerance genes; metal tolerance genes; and drug resistance genes, such as that providing resistance to methotrexate (see e.g., U.S. Pat. No. 5,179,017), among others. Suitable antibiotic resistance genes include any antibiotic resistance marker now known or developed in the future, including (without limitation) markers that confer resistance to ampicillin (e.g., beta-lactamase [bla, TEM-1]), hygromycin (e.g., hygromycin phosphotransferase [aphIV, hpt]), kanamycin, neomycin (e.g., neomycin phosphotransferase II [nptII, APH(3')-II]), chloramphenicol (e.g., chloramphenicol acetyltransferase [$cm^R$, cat]), tetracycline ($tet^R$), and the like. Suitable auxotrophic complementation genes include those involved in DNA-precursor, amino-acid, or cell-wall biosynthetic pathways. Examples of suitable auxotrophic complementation genes include, without limitation, asd (encoding aspartate beta-semialdehyde dehydrogenase), thyA (encoding thymidylate synthetase), glnA (encoding glutamine synthase), leuD (encoding isopropylmalate isomerase small subunit), pyrF (encoding orotidine-5'-phosphate decarboxylase), proC (encoding pyrroline-5-carboxylate reductase), glyA (encoding serine hydroxymethyl transferase), and nadC (encoding quinolinic acid phosphoribosyltransferase), These genes can complement hosts that are auxotrophic for particular nutrients or factors as a result of a disruption of a corresponding chromosomal gene in the host.

Screenable response genes are genes that confer the ability to identify a host expressing the gene and distinguish such hosts from those that do not express the gene. Screenable response genes typically produce products that emit a signal, such as a light signal, in response to a stimulus or a chemical precursor. For example, some response-gene products emit light signals upon irradiation with certain wavelengths of light. Other response-gene products catalyze a reaction wherein the reaction product emits light. The signals produced by the screenable response-gene products are preferably unique signals and are preferably detectable in real-time. These genes include (by way of example only) genes that express chromophoric proteins; genes that signaling proteins and/or regulatory proteins; genes that express detectable surface markers such as CD8; genes that express fluorescent proteins such as green-fluorescent protein, red-fluorescent protein, etc.; luciferase genes; the lacZ gene; the alkaline phosphatase gene; and variants thereof.

Other various examples of response genes include genes involved mutagenesis, carcinogenesis, or onset or alleviation of any given disease state; genes encoding enzymes, such as the CAD gene (see, e.g., Wahl et al., *Somat. Cell Mol. Genet.* 12:339 (1986), among others; genes involved in metabolism, such as amino acid metabolism; genes influencing phytohormone production, and the like.

Figure 2A:
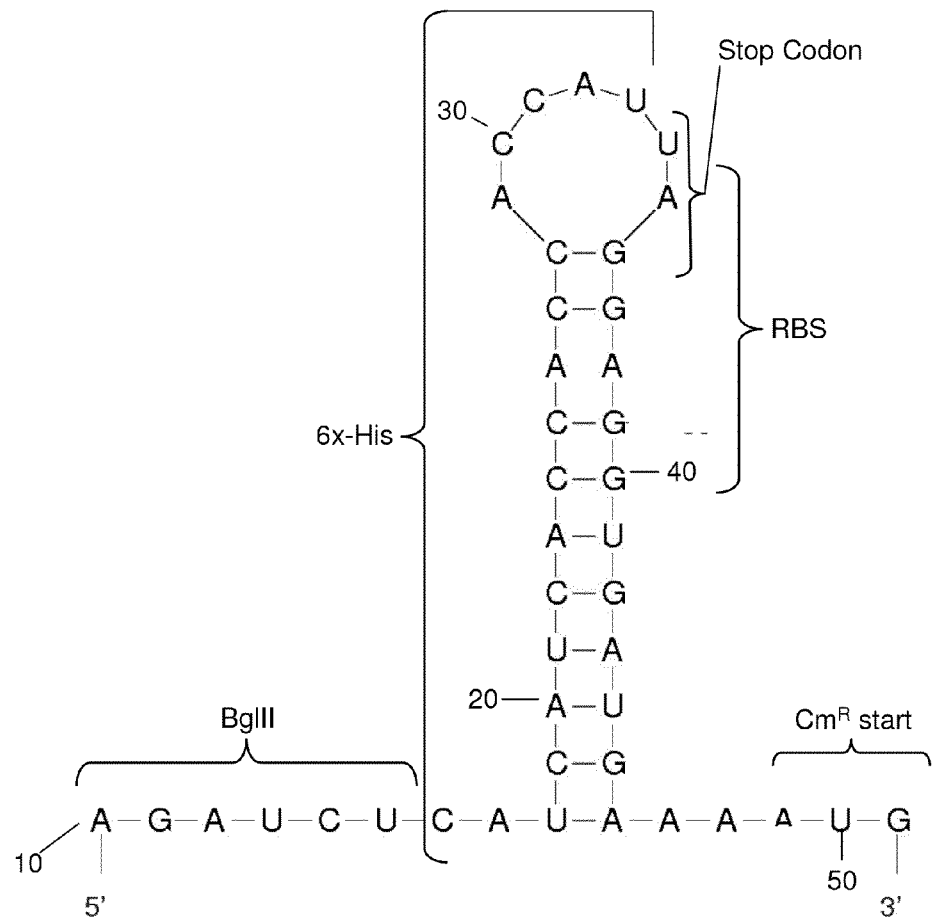
FIG. 2A depicts a portion (bases 10-51) of a translation-coupling cassette identified herein as "TC1" (SEQ ID NO: 1; see Table 1), which includes a downstream portion of a cloning site (BglII; bases 10-15), a protein tag-encoding sequence (6×-His tag; bases 16-33), a stop codon (bases 34-36), a response-gene translation control element (RBS; bases 35-40), a linker (bases 41-48), a start codon of a response gene ($Cm^R$ start; bases 49-51), and a secondary structure-encoding sequence (bases 18-46).
Figure 2B:
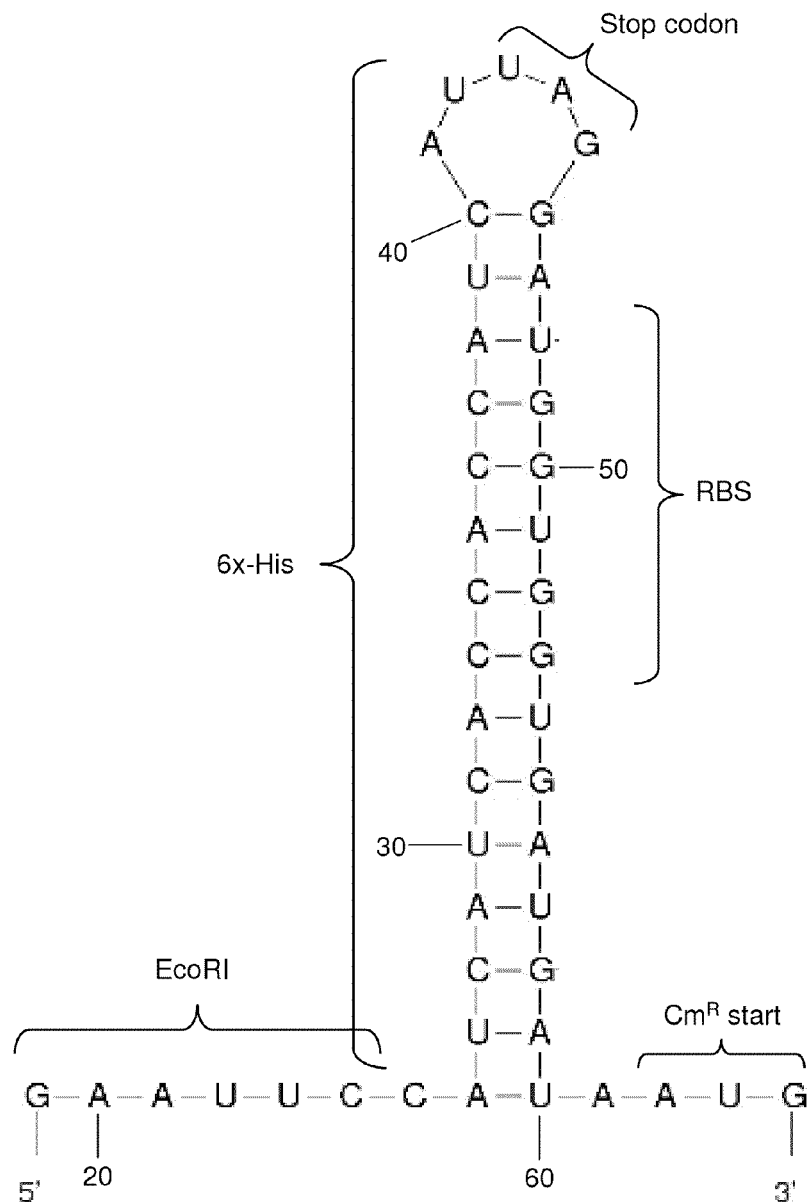
FIG. 2B depicts a portion (bases 19-64) of a translation-coupling cassette identified herein as "TC2" (SEQ ID NO: 2; see Table 1), which includes a downstream portion of a cloning site (EcoRI; bases 19-24), a protein tag-encoding sequence (6×-His tag; bases 25-42), a stop codon (bases 43-45), a response-gene translation control element (RBS; bases 48-53), a linker (bases 54-61), a start codon of a response gene ($Cm^R$ start; bases 62-64), and a secondary structure-encoding sequence (bases 26-60).
Figure 2C:
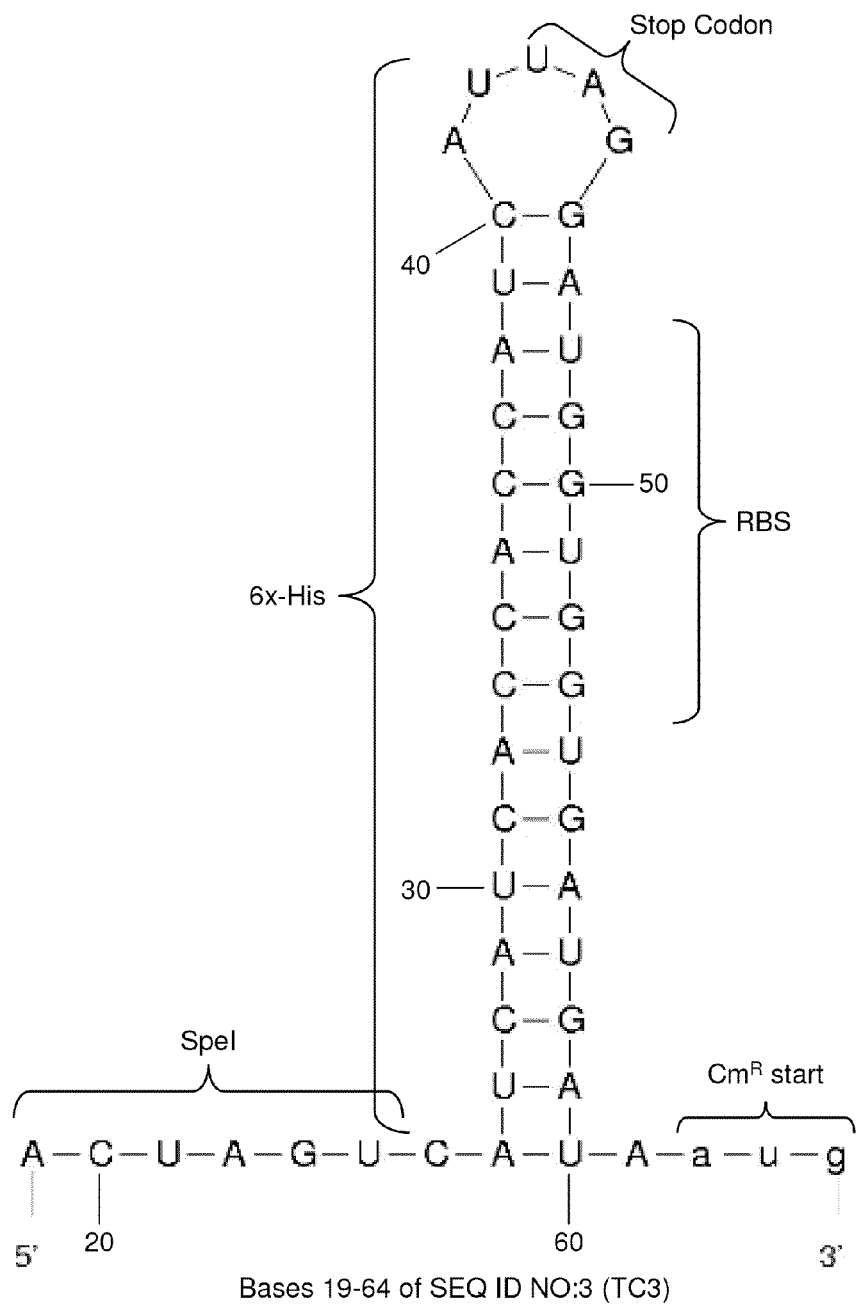
FIG. 2C depicts a portion (bases 19-64) of a translation-coupling cassette identified herein as "TC3" (SEQ ID NO: 3; see Table 1), which includes a downstream portion of a cloning site (SpeI; bases 19-24), a protein tag-encoding sequence (6×-His tag; bases 25-42), a stop codon (bases 43-45), a response-gene translation control element (RBS; bases 48-53), a linker (bases 54-61), a start codon of a response gene ($Cm^R$ start; bases 62-64), and a secondary structure-encoding sequence (bases 26-60).
Figure 2D:
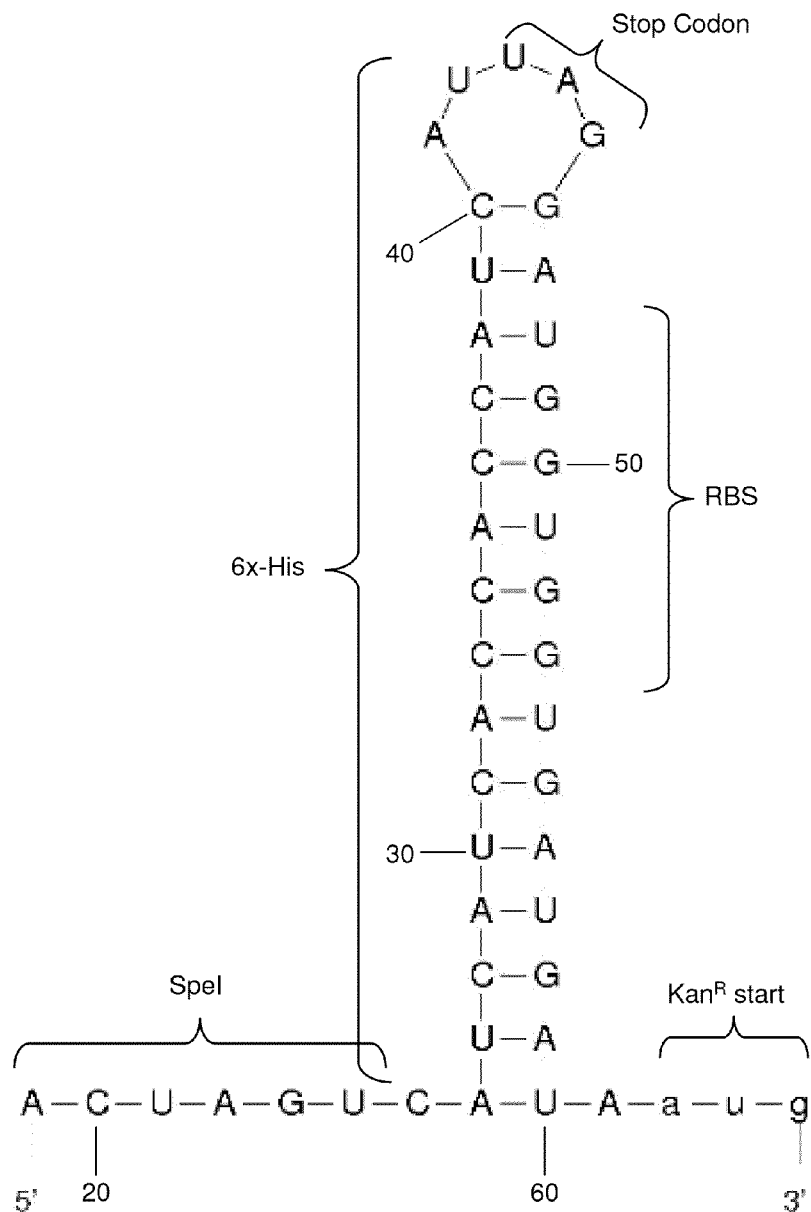
FIG. 2D depicts a portion (bases 19-64) of a translation-coupling cassette identified herein as "TC4" (SEQ ID NO: 4; see Table 1), which includes a downstream portion of a cloning site (SpeI; bases 19-24), a protein tag-encoding sequence (6×-His tag; bases 25-42), a stop codon (bases 43-45), a response-gene translation control element (RBS; bases 48-53), a linker (bases 54-61), a start codon of a response gene ($Kan^R$ start; bases 62-64), and a secondary structure-encoding sequence (bases 26-60).

Non-limiting examples of response genes and their placement with respect to the other elements within the translation-coupling cassette include the chloramphenicol coding sequences at positions 49-708 in SEQ ID NO:1 (see FIG. 2A), positions 62-721 in SEQ ID NO:2 (see FIG. 2B), positions 62-721 in SEQ ID NO:3 (see FIG. 2C), and the kanamycin coding sequence at positions 62-871 in SEQ ID NO:4 (see FIG. 2D). See also the start codon and early coding sequence for the kanamycin resistance gene at positions 47-49 in SEQ ID NO:5 (see FIG. 2E).

In some versions of the invention, the translation-coupling cassette includes a response-gene cloning site in place of a response gene for inclusion of any response gene desired by a user. The response-gene cloning site may comprise any sequence of nucleic acid residues amenable to insertion, by any method, of a response gene therein and may include all those described herein for the target-gene cloning site. As with the target-gene cloning site, the response-gene cloning site may comprise a single restriction site, an MCS, or a ligation-independent cloning site. If the translation-coupling cassette comprises both a target-gene cloning site and a response-gene cloning site, it is preferred that the target-gene cloning site and the response-gene cloning site are different and complementary.

In a preferred version of the invention, the inserted target gene, the inserted response gene, and any intervening sequences therebetween are operably connected to only one promoter, wherein the one promoter is capable of inducing transcription of the inserted target gene, the inserted response gene, and the intervening sequences. In this manner, the translation-coupling cassette is capable of producing a polycistronic RNA transcript and constitutes an artificial operon. The promoter is preferably disposed upstream of the target gene or target-gene cloning site. The promoter can be included in a vector (see below) harboring the translation-coupling cassette at a position upstream of the target gene or the target-gene cloning site for subsequent operable linkage with an inserted target gene. Alternatively, the promoter can be incorporated into the target-gene cloning site of the translation-coupling cassette along with the target gene, provided that a vector harboring the translation-coupling cassette does not already have a promoter operably connected to the target-gene cloning site. Any promoter suitable for transcription in a host in which the translation-coupling cassette is intended to be introduced may be used (see below). Depending on the host, any of a number of suitable control elements, such as transcription enhancer elements (see e.g., Bitter et al. (1987) *Methods in Enzymology*, 153:516-544), can be included in the translation-coupling cassette if not already included in a vector harboring the translation-coupling cassette. Alternatively, the control elements can be in the vector harboring the translation-coupling cassette.

The response gene is preferably operably linked to a sequence encoding a response-gene translation control element. As used herein, "response-gene translation control element" refers to a sequence responsible for controlling translation of the response gene. "Response-gene translation control element" is generally used herein to refer both to the element on the DNA translation-coupling cassette and the corresponding element on the on the RNA transcript thereof, unless explicitly stated otherwise or otherwise implied by the context. The response-gene translation control element is distinct from the element controlling translation of the target gene. The response-gene translation control element can comprise any sequence known or hereafter discovered that induces translation of a gene when exposed but does not induce translation of a gene when masked or otherwise unexposed.

In a preferred version of the invention, the response-gene translation control element is a ribosome binding site. A ribosome binding site is a sequence on an RNA transcript that binds a ribosome in initiating polypeptide translation. Examples of ribosome binding sites include the Shine-Dalgarno sequence and an AU-rich sequence.

The Shine-Dalgarno sequence has the consensus sequence AGGAGG and is generally located about 8-10 bases upstream of the start codon of the response gene whose translation it controls. Many variants of the AGGAGG consensus are known in the art and can be used as a ribosome binding site in the translation-coupling cassette described herein. For example, the sequence in *E. coli* is AGGAGGU. Other variants include GGAG, GGGUGGU, AGGA, UAAGGA, GGAGG, GGGGU, AGGAG, GAG, AGGG, and TGGTGG. See also, Shultzaberger et al. *Journal of Molecular Biology* (2001) 313(1):215-228. The region between the downstream end of the response-gene translation control element, such as the ribosome binding site, and either the response-gene cloning site or the start codon of the response gene is referred to herein as a "linker." A linker for the Shine-Dalgarno sequence or variants thereof can include a number of bases from about 1 to about 20, inclusive, such as about 8-10 bases, and can comprise any sequence. The length of the linker can be optimized in certain hosts for optimal translation of the response gene.

Figure 2E:
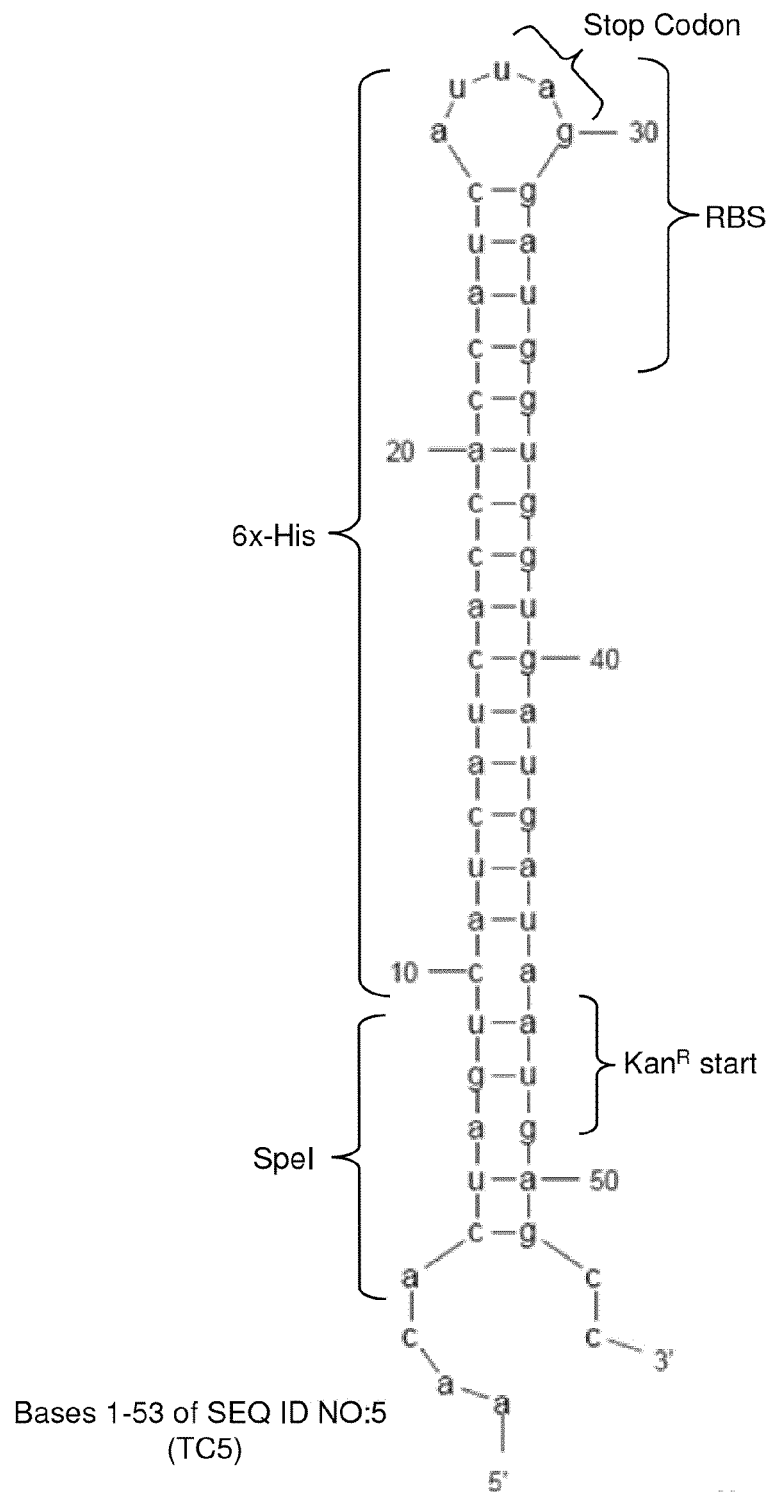
FIG. 2E depicts a portion (bases 1-53) of another translation-coupling cassette identified herein as "TC5" (SEQ ID NO: 5; see Table 1), which includes a downstream portion of a cloning site (SpeI; bases 4-9), a protein tag-encoding sequence (6×-His tag; bases 10-27), a stop codon (bases 28-30), a response-gene translation control element (RBS; bases 29-34), a linker (bases 35-46), an upstream coding sequence of a response gene ($kan^R$ start and onward; bases 47-53), and a secondary structure-encoding sequence (bases 5-51).

Non-limiting examples of response-gene translation control elements as ribosome binding sites and their placement with respect to the other elements in the translation-coupling cassettes of the present invention are included herein as bases 35-40 in SEQ ID NO:1 (AGGAGG; see FIG. 2A), bases 48-53 in SEQ ID NO:2 (TGGTGG; see FIG. 2B), bases 48-53 in SEQ ID NO:3 (TGGTGG; see FIG. 2C), bases 48-53 in SEQ ID NO:4 (TGGTGG; see FIG. 2D), and bases 29-34 in SEQ ID NO:5 (AGGAUG; see FIG. 2E).

Non-limiting examples of linkers, their lengths, and their placement with respect to the other elements in the translation-coupling cassettes of the present invention are included herein as bases 41-48 in SEQ ID NO:1 (see FIG. 2A), bases 54-61 in SEQ ID NO:2 (see FIG. 2B), bases 54-61 in SEQ ID NO:3 (see FIG. 2C), 54-61 in SEQ ID NO:4 (see FIG. 2D), and bases 35-46 in SEQ ID NO:5 (see FIG. 2E).

AU-rich sequences serve as binding sites for the 51 ribosomal protein of the prokaryotic ribosome. Examples of various AU-rich sequences include UAUAAAA, AACACUA, UAUAAAA, AACACUA, AAACACAU, AAUAAAAU, UUAACCUUA, and UUAACUUUA. Other AU-rich sequences are well known in the art. See, e.g., Durand et al. *Nucleic Acids Research* (2006) 34(22):6549-6560 and India et al. *J. Bacteriol.* (2007) 189(11):4028-4037. Any of these sequences can be used in the present invention. The AU-rich sequence is preferably separated from the start codon of the response gene by a linker comprising a number of bases from about 1 to about 50 bases, inclusive, such as about 15 to about 30 bases.

The translation-coupling cassette of the present invention preferably includes a secondary structure-forming sequence. This is a sequence on the translation-coupling cassette that, when transcribed into a corresponding RNA transcript, reversibly forms a secondary structure. The secondary structure-forming sequence is preferably disposed on the translation-coupling cassette with respect to the response gene-control element such that formation of the secondary structure masks the response gene-control element, thereby inhibiting translation of the response gene. If the response gene-control element is a ribosome binding site, formation of the secondary structure blocks ribosome binding thereto and thereby prevents initiation of translation. In a preferred version of the invention, at least part of the response gene-control element overlaps with the secondary structure-forming sequence. However, other configurations are acceptable. For example, the response gene-control element may be wholly subsumed within the secondary structure-forming sequence, or the secondary structure-forming sequence may be wholly subsumed within the response gene-control element. In yet another configuration, the response gene-control element and the secondary structure-forming sequence do not overlap at all, so long as the elements are mutually disposed such that the presence of the secondary structure on the translation-coupling cassette transcript occludes ribosome binding to the ribosome binding site or otherwise inhibits induction of translation via the response gene-control element.

The secondary structure-forming sequence may comprise any sequence of nucleotides that yields a secondary structure that masks, occludes, or otherwise inhibits the function of the response gene-control element in inducing expression. Examples of various elements of RNA secondary structure include stacks, hairpin loops, bulges, internal loops, junctions, and multiloops. Secondary structure-forming sequences can be generated using RNA structure prediction software. Many versions of such software are well-known in the art and include, by way of example, RNAfold, RNAshapes, Pknots, Mfold, among others. In a preferred version of the invention, the formed secondary structure comprises a stem loop, also known as a hairpin loop or hairpin.

Formation of a stem loop can be accomplished when the DNA sequence downstream of the target gene is designed to cause formation of an intra-molecular double-helix in the corresponding RNA transcript. This occurs when two regions of the same strand base-pair to form a double helix that ends in an unpaired loop. The double helix forms the "stem" portion of the stem loop and the unpaired loop forms the loop portion. Sequences that yield stem-loop structures typically include a downstream segment that is substantially a reverse complement of an upstream segment, which together enable intra-molecular base pairing. For example, an AAGC upstream sequence may base pair with a GCUU downstream sequence. The stability of this helix is determined by its length, the number of mismatches or bulges it contains (a small number are tolerable, especially in a long helix), and the base composition of the paired region. Pairings between G and C have three hydrogen bonds and are more stable compared to A-U pairings, which have only two hydrogen bonds. The stability of the unpaired loop portion of the stem-loop structure also influences the formation of the stem-loop structure. Loops that are fewer than three bases long are sterically hindered and do not form. Large loops with no secondary structure of their own (such as pseudo-knot pairing) are also unstable. Optimal loop length tends to be from about four (4) to about ten (10) bases. Base stacking interactions, which align the pi orbitals of the bases' aromatic rings in a favorable orientation, also promote stability. One common loop having the sequence UUCG is particularly stable due to the base-stacking interactions of its component nucleotides.

Preferred secondary structure-forming sequences include reverse-complementary sequences separated by from about four to about ten bases that define a loop portion when the reverse-complementary sequences bind to define the stem portion of the stem-loop structure. Non-limiting examples of secondary structure-forming sequences, specifically stem loops, and their positions with respect to the other elements in the translation-coupling cassette are included as positions 18-46 in SEQ ID NO:1 (see FIG. 2A), positions 26-60 in SEQ ID NO:2 (see FIG. 2B), positions 26-60 in SEQ ID NO:3 (see FIG. 2C), positions 26-60 in SEQ ID NO:4 (see FIG. 2D), and positions 5-51 in SEQ ID NO:5 (see FIG. 2E).

In the preferred version of the invention, at least a portion of the secondary structure-forming sequence is translationally linked with the target-gene cloning site or the target gene. One version of a translation-coupling cassette having at least a portion of the secondary structure-forming sequence translationally linked with the target-gene cloning site or target gene includes a stop codon within or downstream of the secondary structure-forming sequence. Translation of a pre-existing target gene or target gene subsequently inserted in the target-gene cloning site will comprise translation of the target gene, any intervening sequences between the target gene and the secondary structure-forming sequence, and portions or all of the secondary structure-forming sequence up to the stop codon. The stop codon and any pre-existing target gene in the expression vector should be in-frame. Similarly, any target gene inserted in a target-gene cloning site should be inserted in-frame with the stop codon.

In a preferred version of the invention, the stop codon is included within the secondary structure-forming sequence. Further, if the secondary structure-forming sequence is configured to form a stem loop, the stop codon may be included within an upstream segment of the stem portion of the stem loop, within the loop portion of the stem loop, or within a downstream segment of the stem portion of the stem loop. (See FIG. 1B for loop portion 34 of the stem loop 30, upstream segment 32, and downstream segment 36.) This positioning ensures unwinding of the stem loop and unmasking of the response-gene translation control element during translation of the target gene (see examples). The preferred locations of the stop codon in the stem loop and its positioning with respect to the response-gene translation control element are as shown in FIGS. 2A-E.

In yet other versions, the stop codon may be included upstream of the secondary structure-forming sequence.

Non-limiting examples of stop codons translationally linked with the target genes or target gene cloning sites and their positions with respect to the other elements in the translation-coupling cassette are included as bases 34-36 in SEQ ID NO:1 (see FIG. 2A), bases 43-45 in SEQ ID NO:2 (see FIG. 2B), bases 43-45 in SEQ ID NO:3 (see FIG. 2C), bases 43-45 in SEQ ID NO:4 (see FIG. 2D), and bases 28-30 in SEQ ID NO:5 (see FIG. 2E).

The translation-coupling cassette may further include a sequence encoding a protein tag that is either translationally linked with a target-gene cloning site or in-frame and translationally linked with a target gene. Thus, translation of the pre-existing target gene or any target gene inserted in-frame in the target-gene cloning site includes translation of the protein tag as a sub-domain of the translated target-gene product. Fusion of a protein tag in this manner can be useful in any number of applications using the product expressed from the target gene, including purification via immunoprecipitation or affinity chromatography, detection via immunoblotting, or real-time detection. Non-limiting examples of suitable protein tags include chitin binding protein (CBP), maltose binding protein (MBP), glutathione-S-transferase (GST), poly(His) tag, thioredoxin (TRX), poly(NANP), FLAG tag, V5 tag, c-myc tag, HA tag, fluorescent tags such as green fluorescent protein (GFP) or red fluorescent protein (RFP), biotin ligase tag, isopeptag, biotin carboxyl carrier protein, S tag, strep tag, and SBP tag.

In a preferred version of the invention, at least a portion of the protein tag-encoding sequence is included as part of the secondary structure-forming sequence. A preferred sequence for this purpose is a sequence encoding a poly(His) tag, such as a 6×-His tag.

Non-limiting examples of protein-tag encoding sequences (encoding 6×-His tags) translationally linked with the target genes or target gene cloning sites and their positions with respect to the other elements in the translation-coupling cassette are included as bases 16-33 in SEQ ID NO:1 (see FIG. 2A), bases 25-42 in SEQ ID NO:2 (see FIG. 2B), bases 25-42 in SEQ ID NO:3 (see FIG. 2C), bases 25-42 in SEQ ID NO:4 (see FIG. 2D), and bases 10-27 in SEQ ID NO:5 (see FIG. 2E).

Operation of an exemplary version of the translation-coupling cassette of the present invention is as follows. The exemplary translation-coupling cassette includes a target gene, a response gene, a response-gene translation control element, and a secondary structure-forming sequence, wherein at least part of the secondary structure-forming sequence is translationally linked with the target gene. Transcription of such a translation-coupling cassette generates an mRNA transcript with corresponding genetic elements, wherein the secondary structure in the secondary structure-forming sequence is formed in the absence of active or complete translation of the target gene. When the target gene is fully translated, the ribosome also translates any downstream sequences translationally linked to the target gene up to the first in-frame stop codon. In the process of translation, the ribosome also translocates along the same sequences, unwinding the RNA secondary structure that reversibly forms in the absence of translation. Flattening the RNA secondary structure exposes the response-gene translation control element and permits translation of the response gene. In cases in which the response-gene translation control element is a ribosome binding site, flattening of the RNA structure permits access of the ribosome to bind to the ribosome binding site to initiate translation. In this manner, full translation of the target gene results in translation of the response gene. Disrupted or otherwise incomplete translation of the target gene, however, results in inhibited translation of the response gene due to masking of the response-gene translation control element.

Hosts that fully translate the target gene are identified by detecting the presence of the response-gene protein product, either directly or indirectly. For example, if the response gene is an antibiotic resistance response gene, the transformed hosts that fully translate the target gene are resistant to the corresponding antibiotic. If the response gene is a fluorescent protein response gene, the transformed hosts that fully translate the target gene fluoresce at the wavelength corresponding to the response-gene product. If the response gene is an enzyme-encoding gene, the transformed hosts that fully translate the target gene demonstrate the enzymatic activity of the response-gene product. If the response gene is a gene encoding a regulatory protein, the transformed hosts that fully translate the target gene demonstrate the additional regulatory activity.

If the product of the target gene is not fully translated, the response gene is also not translated because the secondary structure in the mRNA transcript remains intact. The secondary structure in the mRNA therefore masks or occludes the response-gene translation control element. Transformed hosts that do not successfully translate the target gene do not display the characteristics of the gene product of the response gene. That is, if the response gene is an antibiotic resistance gene, the transformed hosts are sensitive to antibiotic rather than resistant to it. If the response gene is a fluorescent protein response gene, the transformed hosts do not fluoresce at the wavelength corresponding to the response-gene product. If the response gene is an enzyme-encoding gene, the transformed cells do not demonstrate the enzymatic activity of the response-gene product. If the response gene encodes a regulatory protein, the transformed hosts do not demonstrate the additional regulatory activity.

Figure 1A:
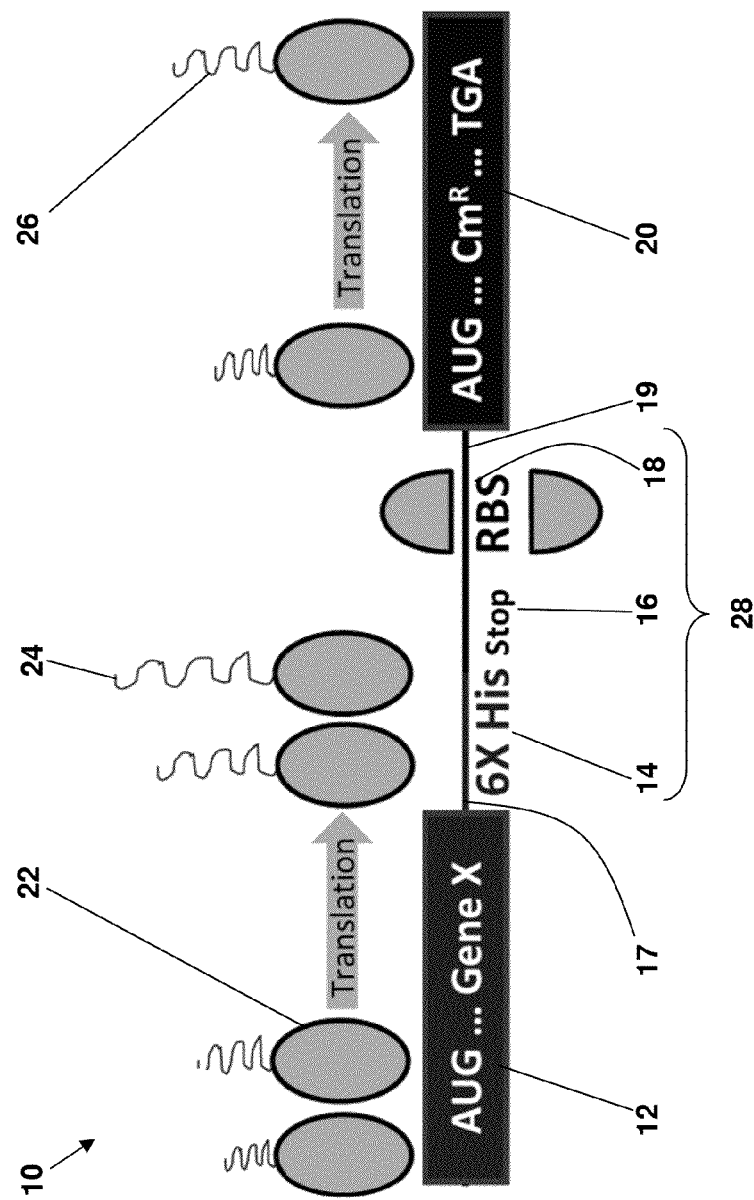
FIG. 1A depicts an mRNA transcript of a translation-coupling cassette of the present invention with full translation of a target gene, disruption of RNA secondary structure, and consequent translation of a response gene.
Figure 1B:
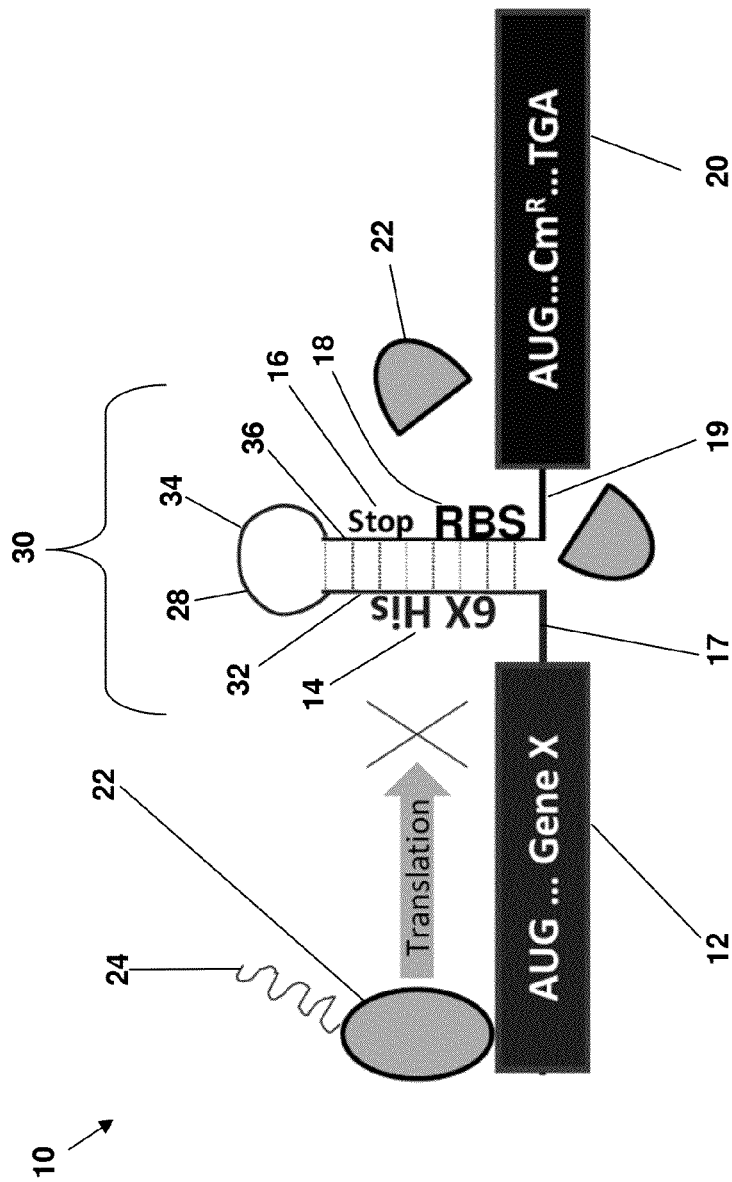
FIG. 1B depicts the mRNA transcript of FIG. 1A with incomplete translation of the target gene, masking of a ribosome binding site by RNA secondary structure, and inhibition of response gene translation.

An illustrative mRNA transcript 10 of a translation-coupling cassette of the present invention is depicted in FIGS. 1A and 1B. The depicted transcript 10 includes a target gene 12 (AUG . . . Gene X) followed by a downstream portion of a target-gene cloning site 17 and a translationally linked and in-frame protein tag-encoding sequence 14 (6x-His) and stop codon 16 (Stop). A separate ribosome binding site controlling translation of the target gene 12 is not shown. The depicted transcript 10 also includes a response gene 20 (AUG . . . Cm$^R$ . . . TGA) preceded by a ribosome binding site 18 (RBS) controlling expression of the response gene 20. Interspersed between the ribosome binding site 18 and the response gene 20 is a linker 19. The protein tag-encoding sequence 14, the stop codon 16, and the ribosome binding site 18 together form a secondary structure-forming sequence 28.

FIG. 1A depicts complete translation of the target gene 12 coupled with translation of the response gene 20. Shown are ribosomes 22 translating the target gene 12 through to the translationally linked protein tag-encoding sequence 14 and translocating to the stop codon 16. The complete translation of the target gene 12 disrupts RNA secondary structure, such as a stem loop 30 that otherwise occludes the ribosome binding site 18 of the response gene 20 (see FIG. 1B). Disrupting the secondary structure exposes the ribosome binding site 18 and thereby enables translation of the response gene 20. As a result, both the target-gene product 24 and the response-gene product 26 are fully translated. Successfully transformed hosts are then selected and/or identified based on the characteristics of the expressed gene product 26 of the response gene 20.

FIG. 1B depicts interrupted or incomplete translation of the target gene 12. Here, the target gene 12 is not fully translated to its corresponding gene product 24, and the ribosome 22 fails to translocate through to the protein tag-encoding sequence 14 and the stop codon 16. The failure to fully translocate enables formation of a secondary structure. The depicted secondary structure is a stem loop 30 that includes a stem portion, defined by an upstream segment 32 and a downstream segment 36, and a loop portion 34 between the upstream segment 32 and the downstream segment 36. The upstream segment 32 of the stem portion in the present example comprises the protein tag-encoding sequence 14, and the downstream segment 36 comprises the stop codon 16 and the ribosome binding site 18. Formation of the stem loop 30 blocks access of the ribosome 22 to the ribosome binding site 18 and thereby prevents translation of the response gene 20.

The translation-coupling cassette of the present invention can be included in a vector. As used herein, "vector" refers to an entity comprising the translation-coupling cassette that is capable of introducing the translation-coupling cassette into a host for transcription of the translation-coupling cassette and translation of any encoded genes. The vector can include nucleic acid sequences that permit it to replicate in the cell, such as an origin of replication. The vector can also include a promoter upstream of the target-gene cloning site or target gene or other regulatory elements such as enhancers to initiate transcription of the translation-coupling cassette. The vector can further include translational control sequences, such as a ribosome binding site and/or upstream AT-rich sequences, operably connected to the target gene or target gene cloning site. The vector can also include one or more selectable marker genes independent of the response gene to isolate hosts harboring the vector. Suitable expression vectors include, but are not limited to viral vectors, such as those based on baculovirus, vaccinia virus, polio virus, adenovirus, adeno-associated virus, SV40, herpes simplex virus, and the like; phage vectors, such as bacteriophage vectors; plasmids; phagemids; cosmids; fosmids; bacterial artificial chromosomes; Pl-based artificial chromosomes; yeast plasmids; yeast artificial chromosomes; and any other vectors specific for hosts of interest (such as *E. coli, Pseudomonas pisum*, or *Saccharomyces cerevisiae*). Commercially available vectors for expressing heterologous proteins in bacterial hosts that provide elements for inclusion in the vector of the present invention include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx.

Some versions of the invention include hosts that comprise the translation-coupling cassette, such as hosts that comprise a vector harboring the translation-coupling cassette. Suitable hosts include any cells or cell-free systems that contain the appropriate molecular machinery to transcribe the translation-coupling cassette and translate the genes encoded therein. With respect to translation, the host must contain the appropriate molecular machinery for operation with the particular response-gene translation control element, such as the ribosome binding site.

The ribosome binding sites disclosed herein are derived from microbes, and more specifically, prokaryotic microbes. Therefore, the preferred host is a prokaryotic host. Examples of suitable prokaryotic hosts include Gram-positive bacteria such as strains of *Bacillus*, (e.g., *B. brevis* or *B. subtilis*), *Pseudomonas*, or *Streptomyces*, or Gram-negative bacteria, such as strains of *E. coli*. Particularly desirable hosts in this regard include bacteria that do not produce lipopolysaccharide and are, therefore, endotoxin free.

Although not preferred, the host may also be a eukaryotic host. For the eukaryotic host to employ prokaryotic-derived ribosome binding sites in the translation-coupling cassette, the host must express the appropriate molecular machinery. The appropriate molecular machinery may include a prokaryotic ribosome and the initiation factors required for initiation of prokaryotic translation. The appropriate molecular machinery may further include elongation and release factors required for elongation and termination, respectively, of prokaryotic translation. Suitable eukaryotic hosts include such yeast hosts as strains of *Saccharomyces*, such as *S. cerevisiae; Schizosaccharomyces; Kluyveromyces; Pichia*, such as *P. pastoris* or *P. methlanolica; Hansenula*, such as *H. Polymorpha; Yarrowia*; or *Candida*. Other suitable eukaryotic hosts include such filamentous fungal hosts as strains of *Aspergillus*, e.g., *A. oryzae, A. niger*, or *A. nidulans; Fusarium* or *Trichoderma*. Other suitable eukaryotic hosts include such insect hosts as a Lepidoptora cell line, such as *Spodoptera frugiperda* (Sf9 or Sf21) or *Trichoplusioa ni* cells ("HIGH FIVE"-brand insect cells, Invitrogen, Carlsbad, Calif.) (U.S. Pat. No. 5,077,214). Yet other suitable eukaryotic hosts include such mammalian hosts as Chinese hamster ovary (CHO) cell lines, e.g., CHO-K1 (ATCC CCL-61); green monkey cell lines, e.g., COS-1 (ATCC CRL-1650) and COS-7 (ATCC CRL-1651); mouse cells, e.g., NS/O; baby hamster kidney (BHK) cell lines, e.g., ATCC CRL-1632 or ATCC CCL-10; and human cells, e.g., HEK 293 (ATCC CRL-1573). Additional suitable cell lines are known in the art and available from public depositories such as the American Type Culture Collection, Rockville, Md.

A suitable host can be produced by introducing the translation-coupling cassette in it. As used herein, "introduce," used with reference to introducing the translation-coupling cassette into a host, refers to the delivery of the translation-coupling cassette to the host in a manner such that any genes encoded by the translation-coupling cassette are capable of being transcribed and translated within the host. Thus, introducing a translation-coupling cassette in a host suitably includes introducing a vector comprising the translation-coupling cassette in the host. Introducing the translation-coupling cassette can be performed by both transformation and transfection. Transformation encompasses techniques by which the translation-coupling cassette is introduced into hosts such as prokaryotic cells or non-animal eukaryotic cells. Transfection encompasses techniques by which the translation-coupling cassette is introduced into hosts such as animal cells. These techniques include but are not limited to introduction of the translation-coupling cassette via conjugation, electroporation, lipofection, infection, and particle gun acceleration. The introduction of a vector into a bacterial host may, for instance, be performed by protoplast transformation (Chang and Cohen (1979) *Molecular General Genetics*, 168: 111-115), using competent cells (Young and Spizizen (1961) *Journal of Bacteriology*, 81:823-829; Dubnau and Davidoff-Abelson (1971) *Journal of Molecular Biology*, 56: 209-221), electroporation (Shigekawa and Dower (1988) *Biotechniques*, 6:742-751), or conjugation (Koehler and Thorne (1987) *Journal of Bacteriology*, 169:5771-5278). Methods of introducing vectors into the eukaryotic hosts are well-known in the art.

Suitable promoters for use in prokaryotic hosts include but are not limited to: promoters capable of recognizing the T4, T3, Sp6, and T7 polymerases; the $P_R$ and $P_L$ promoters of bacteriophage lambda; the trp, recA, heat shock, araBAD, propionate, trc, tac, tac-lac, tet, constitutive sigma 70, and lacZ promoters of *E. coli*, as well as any artificial promoter selected from engineered libraries (see Alper et al. (2005) *PNAS* 102(36):12678-83); the alpha-amylase and the sigma-specific promoters of *B. subtilis*; the promoters of the bacteriophages of *Bacillus; Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, $3^{rd}$ ed., Cold Spring Harbor Laboratory Press (2001).

Suitable promoters for use within a eukaryotic host are typically viral in origin and include, without limitation, the promoter of the mouse metallothionein I gene (Hamer et al. (1982) *J. Mol. Appl. Gen.* 1:273); the TK promoter of Herpes virus (McKnight (1982) Cell 31:355); the SV40 early promoter (Benoist et al. (1981) *Nature* (London) 290:304); the Rous sarcoma virus promoter; the cytomegalovirus promoter (Foecking et al. (1980) Gene 45:101); the yeast gal4 gene promoter (Johnston et al. (1982) *PNAS* (USA) 79:6971; Silver et al. (1984) *PNAS* (USA) 81:5951); and the IgG promoter (Orlandi et al. (1989) *PNAS* (USA) 86:3833).

Inducible, repressible, and constitutive promoters are all suitable for use in the present invention. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-I promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, Calif.); and variants thereof.

Constitutive promoters do not require an effector to initiate transcription. Suitable constitutive promoters are known in the art.

The translation-coupling cassette described herein has many uses. One use comprises a method of assessing whether full-length products of target genes are being produced in a host. This method includes the steps of introducing the translation-coupling cassette into a host and determining the presence or level of response-gene expression. The step of determining the presence or level of response-gene expression is performed by detecting the presence of the product of the response gene, as described herein.

The translation-coupling cassette can also be used to identify culture conditions that increase target protein production. This can be performed by culturing identical hosts in two different culture conditions and comparing the expression levels of the response gene among the various conditions. The variables changed in the different culture conditions may include culture temperatures, particular nutrients, etc.

The translation-coupling cassette can also be used to screen a DNA library for genes that enhance expression of a target gene. Suitable DNA libraries include, without limitation, genomic, cDNA, and metagenomic libraries. The method is performed by introducing a host with two vectors—a first comprising the translation-coupling cassette and a second from a DNA library. Clones from the DNA library that enhance target-gene expression can be identified by screening levels of response-gene expression or by selecting hosts that express a selectable response gene. The effective clones can be identified by sequencing. Possible factors that may facilitate expression of a target gene may include ribosomal components, chaperones, modifying enzymes, translational enhancers, and/or regulatory proteins.

The translation-coupling cassette can also be used to determine if any random sequence of codons will be translated in a chosen host.

The translation-coupling cassette can also be used to select for mutated versions of a target gene for versions that express or express at higher levels. This can be performed by generating various versions of the target gene by error prone PCR or other known mutagenic techniques, cloning the mutated versions of the target genes into translation-coupling cassettes using known techniques, introducing the translation-coupling cassettes into hosts, and comparing the expression level of each version of the target gene by determining the respective levels of response-gene expression.

Optimization of translation of the target gene may require modification of any portion or the entirety of the target gene's coding region, 5' UTR, or other elements therein.

In the coding region, the nucleotide sequence of the target gene can be kept the same as that of the wild-type gene found in the genome of the source organism, or it can be different. Owing to the degeneracy of the genetic code, changes in the nucleotide sequence of the target gene need not necessarily lead to changes in the amino acid sequence of the gene product.

Codons in the coding region may be optimized to increase expression of the target gene in a selected host. One example of optimizing codons includes modifying the codon usage of the coding sequence of the target gene. Although codon usage is not widely believed to impact the translational efficiency of an mRNA in higher eukaryotes, a codon bias similar to that of E. coli does enhance the translational efficiency of heterologous genes in E. coli. Avoiding infrequently-used codons can also lead to enhanced stability of an mRNA because sequences that promote instability of mRNAs often comprise infrequently-used codons. Codon optimization can be performed for any nucleic acid by "OPTIMUMGENE"-brand gene design system by GenScript (Piscataway, N.J.) or any other commercial or proprietary algorithm.

The coding region of the target gene can also be altered to remove or insert restriction enzyme sites. Removal of a restriction enzyme site or sites may be required for successful transformation of restriction-positive prokaryotic hosts which express the corresponding restriction enzyme. Removing or inserting restriction enzyme sites can be performed by site-specific mutagenesis or cassette mutagenesis techniques, which are well known in the art. Regardless, it is generally preferred when using prokaryotic hosts, to use restriction-minus hosts.

Although nucleotide changes in the coding region do not automatically lead to changes in the amino acid sequence of the gene product, the amino acid sequence of the gene product can be changed by changing the nucleotide sequence of the target gene by techniques known in the art. In some cases, a particular amino acid sequence is more amenable to translation in a particular host than other amino acid sequences.

The 5' untranslated regions (UTRs) of a target gene transcript can also be cloned or synthesized, and in either case changed or left intact, by techniques known in the art. Modifying the 5' UTR of the target gene may affect its translational efficiency. The 5' untranslated region (UTR) comprises the ribosome binding site and also plays a role in mRNA stability. Use of a ribosome binding site for the target gene dissimilar to the consensus sequence for ribosome binding sites in the host cell can lead to either reduced rates of translation of the gene product, recognition of cryptic ribosome binding sites elsewhere in the mRNA with subsequent translation of non-desired truncated or frame-shifted proteins, or both. To avoid such unwanted effects, the ribosome binding site of the 5' UTR of the target gene can be modified from its native or original sequence to match or nearly match the consensus sequence for the ribosome binding site in the host cell. Such modification can be affected by site-specific mutagenesis or cassette mutagenesis techniques, both of which are well known in the art. Also, specific sequences in the 5' UTR can enhance or diminish the stability of the mRNA depending on the host cell, and stabilizing sequences can be added and destabilizing sequences removed by the site-specific mutagenesis or cassette mutagenesis techniques. 5' UTR stabilizing and destabilizing sequences in particular host cells are widely known to those of skill in the art.

While in many versions of the translation-coupling cassette described herein the target gene encodes a "protein of interest" for downstream purposes and the response gene serves as an indicator of target gene expression, these roles can be reversed for particular purposes. In one version, a series of translation-coupling cassettes including a detectable (i.e., selectable or screenable) target gene, preferably a fluorescent target gene, is constructed. The target gene of each translation-coupling cassette in the series is driven by a different translational control sequence with known relative efficiency. The translation-coupling cassettes further include a response-gene cloning site for insertion of a gene of interest. With such a system, the response gene can be expressed at a particular desired and pre-determined level corresponding to the strength of the translational control element, which can be verified by a level of emitted fluorescence or other detectable characteristic of the target gene. In such versions, a protein tag may be translationally linked to the response-gene cloning site for ease in purification of the response gene.

In yet another version, the target gene may encode a protein of no particular interest, and the response gene may encode a protein of interest. A series of translation-coupling cassettes may be constructed, each having a secondary structure sequence with a different translational control sequence of known relative efficiency controlling the response gene. As above, a particular translation-coupling cassette can be chosen for use according to the level of translation of the response-gene product desired.

Many of the steps described herein for manipulating and analyzing nucleic acids and proteins, including digesting with restriction endonucleases, amplifying by PCR, hybridizing nucleic acids, ligating nucleic acids, separating and isolating by gel electrophoresis, transforming cells with heterologous DNA, selecting successful transformants, purifying with chromatography, performing Western blots, and the like, are well known and widely practiced by those skilled in the art and are not extensively elaborated upon herein. Unless otherwise noted, the protocols utilized herein are described extensively in Sambrook & Russell (2001), *Molecular Cloning: A Laboratory Manual, Third Edition*; Cold Spring Harbor Laboratory Press: New York, N.Y., ISBN-13: 978-0879695774.

The present invention is, in part, directed to DNA translation-coupling cassettes and RNA transcripts thereof. While DNA primarily includes thymine (T) rather than uracil (U), RNA primarily includes U rather than T. Any disclosure herein of a sequence including T for a DNA translation-coupling cassette also constitutes a disclosure of a corresponding sequence with U in place of T for the RNA transcript. Conversely, any disclosure herein of a sequence including U for an RNA transcript constitutes a disclosure of a corresponding sequence with T in place of U for the DNA translation-coupling cassette. Unless explicitly stated otherwise or indicated otherwise by the context, any genetic element defined in a DNA cassette, e.g., gene, coding sequence, response-gene translation control element, secondary structure-forming sequence, or protein tag-encoding sequence, applies equally to a corresponding element in the RNA transcript, and vice versa.

"Inserting," used in reference to inserting a gene into a cloning site refers to cloning the gene into the cloning site by any method described herein or known in the art.

"Operably linked" is used herein to refer to joined nucleic acid sequences wherein one sequence performs a regulatory operation on another sequence. Nucleic acid sequences which are operationally linked are not necessarily directly contiguous to one another but may be separated by intervening nucleotides which do not interfere with the operational relationship of the linked sequences.

"Translationally linked," used with reference to a first genetic element and a second genetic element, means that the first genetic element and any intervening sequences between the first genetic element and the second genetic element does not include an in-frame stop codon. This means that translation of a first genetic element that is translationally linked with a second genetic element will comprise translation of the first genetic element, any intervening sequences between the first genetic element and the second genetic element, and portions or all of the second element up to the first in-frame stop codon.

"Gene product" or variations thereof is used herein to refer to the polypeptide produced by transcription of a specific DNA coding region into mRNA followed by translation of the mRNA by a ribosome. Such a polypeptide may also be referred to as a "protein." If the gene product functions as a catalyst in a chemical reaction, the gene product may also be referred to as an "enzyme."

"Upstream" and "downstream" are used herein in the sense commonly used in the art to refer to directions toward the 5' end and the 3' end, respectively, of nucleic acid molecules or toward the N-terminus or C-terminus, respectively, of protein molecules.

The elements and method steps described herein can be used in any combination whether explicitly described or not. All combinations of method steps as described herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The tools and methods of the present invention can comprise, consist of, or consist essentially of the essential elements and limitations described herein, as well as any additional or optional steps, components, or limitations described herein or otherwise useful in the art.

It is understood that the invention is not confined to the particular construction and arrangement of parts herein illustrated and described, but embraces such modified forms thereof as come within the scope of the claims.

EXAMPLES

A series of translation-coupling cassettes with target-gene cloning sites and selection markers as response genes were constructed using standard molecular biological techniques. The translation-coupling cassettes and their features are summarized in Table 1, portions of which are shown in FIGS. 2A-E. Plasmid vectors with several of the translation-coupling cassettes and one of several different target genes cloned in the target-gene cloning site were generated, as summarized in Table 2. The plasmids contained the necessary transcriptional and translational control elements for transcription of the translation-coupling cassette and translation of the inserted target gene, respectively. The plasmids were introduced into *E. coli* cells using standard techniques. The transformed cells were cultured in the presence of various levels of selection agent and assessed for cell growth to determine levels of response-gene expression. In addition, target-gene expression levels were assessed by detecting fluorescence emitted by fluorescent target genes (i.e., red fluorescent protein, RFP) and/or purification of the target-gene product via a fused 6x-His tag using Ni-NTA affinity chromatography and analysis by SDS-PAGE.

TABLE 1

Translation-Coupling Cassettes[‡]

| Name | Target-Gene Cloning Site | Response gene | Hairpin Sequence | SEQ ID NO |
|---|---|---|---|---|
| TC1 | BglII, EcoRI; | $Cm^R$ | FIG. 2A | 1 |
| TC2 | BglII, EcoRI; ligation-independent cloning competent | $Cm^R$ | FIG. 2B | 2 |
| TC3 | SpeI, MfeI; | $Cm^R$ | FIG. 2C | 3 |
| TC4 | SpeI, MfeI; | $Kan^R$ | FIG. 2D | 4 |
| TC5 | SpeI | $Kan^R$ | FIG. 2E | 5 |

[‡]$Cm^R$, chloramphenicol resistance marker; $Kan^R$, kanamycin resistance marker

TABLE 2

Plasmids with Various Translation-Coupling Cassettes Comprising Target-Gene Inserts and Observed Phenotypes of Strains Harboring Them[‡]

Figure 7B:
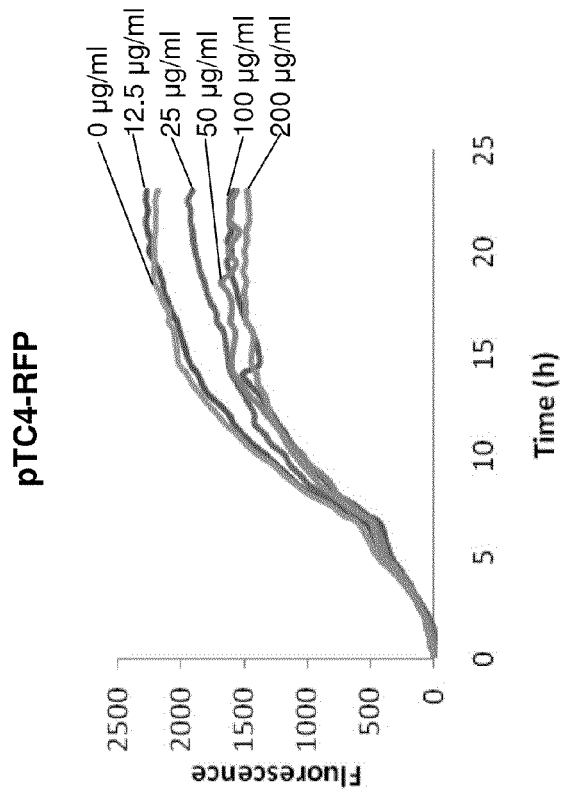
FIGS. 7A and 7B show growth and fluorescence curves, respectively, from *E. coli* cells transformed with the pTC4-RFP plasmid (see Tables 1 and 2) and grown in the presence of the shown concentrations (μg/ml) of kanamycin.
Figure 7A:
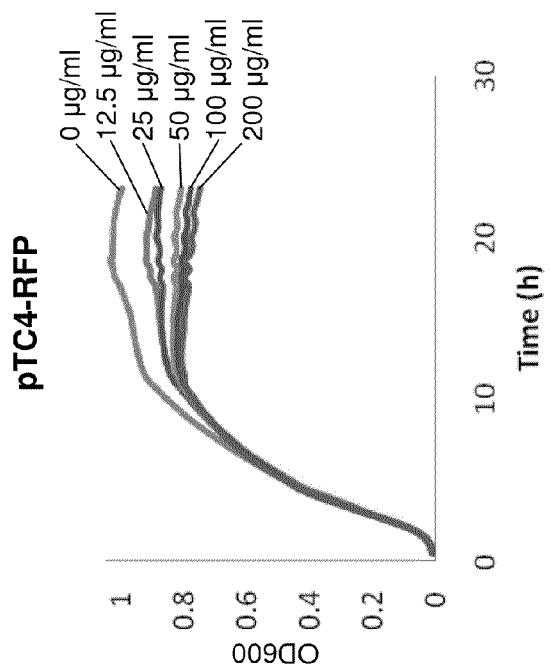

| Plasmid | Translation-Coupling Cassette | Target-Gene Insert | Phenotype Observed |
|---|---|---|---|
| pTC1-RFP | TC1 | RFP | Growth in all Cm concentrations; strong fluorescence; strong RFP protein band (FIGS. 3A-C) |
| pTC1-RFP* | TC1 | RFP* | Weak growth in low Cm; no detectable fluorescence (FIGS. 4A-B) |
| pTC2-RFP | TC2 | RFP | Growth and fluorescence trends inversely with Cm concentration (FIGS. 5A-B) |
| pTC2-RFP* | TC2 | RFP* | No growth; no fluorescence (FIGS. 6A-B) |
| pTC4-RFP | TC4 | RFP | Growth and fluorescence trends inversely with Km concentration (FIGS. 7A-B) |
| pTC4-RFP* | TC4 | RFP* | No growth; no fluorescence (FIGS. 8A-B) |
| pTC4-D1-D8 | TC4 | D1-D8 of Gene X | No growth (FIG. 10) |
| pTC4-D1-D2 | TC4 | D1-D2 of Gene X | Growth; purified protein (FIGS. 11A-B) |
| pTC4-D3-D5 | TC4 | D3-D5 of Gene X | Growth; purified protein (FIGS. 12A-B) |
| pTC4-D6-D8 | TC4 | D6-D8 of Gene X | No growth; no purified protein (FIGS. 13A-B) |

[‡]RFP, full-length red fluorescent protein; RFP*, RFP with premature stop codon; Cm, chloramphenicol; Km, kanamycin As a proof of concept for the expression-coupling system described herein, a first set of experiments was carried out with the TC1 translation-coupling cassette using either full length red fluorescent protein (RFP) gene or an RFP gene with a premature stop codon (RFP*) inserted as the target gene. Vectors harboring each cassette were designated as pTC1-RFP and pTC1-RFP*, respectively (see Table 2). E. coli cells transformed with each plasmid vector were grown in the presence of 34, 61, 89, 116, 144, 171, or 199 µg/ml chloramphenicol.

Figures 4A, 4B:
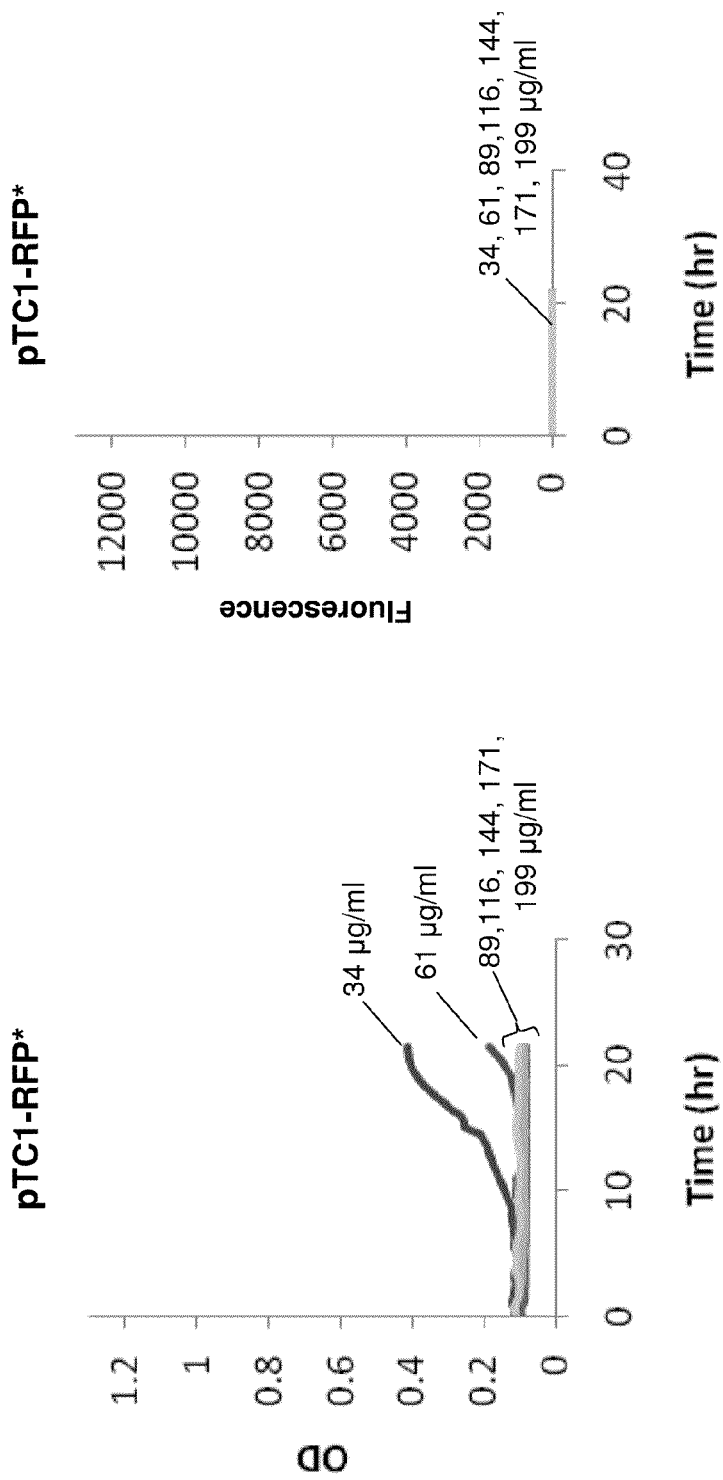
FIGS. 4A and 4B show growth and fluorescence curves, respectively, from *E. coli* cells transformed with the pTC1-RFP* plasmid (see Tables 1 and 2) and grown in the presence of the shown concentrations (μg/ml) of chloramphenicol.
Figures 5A, 5B:
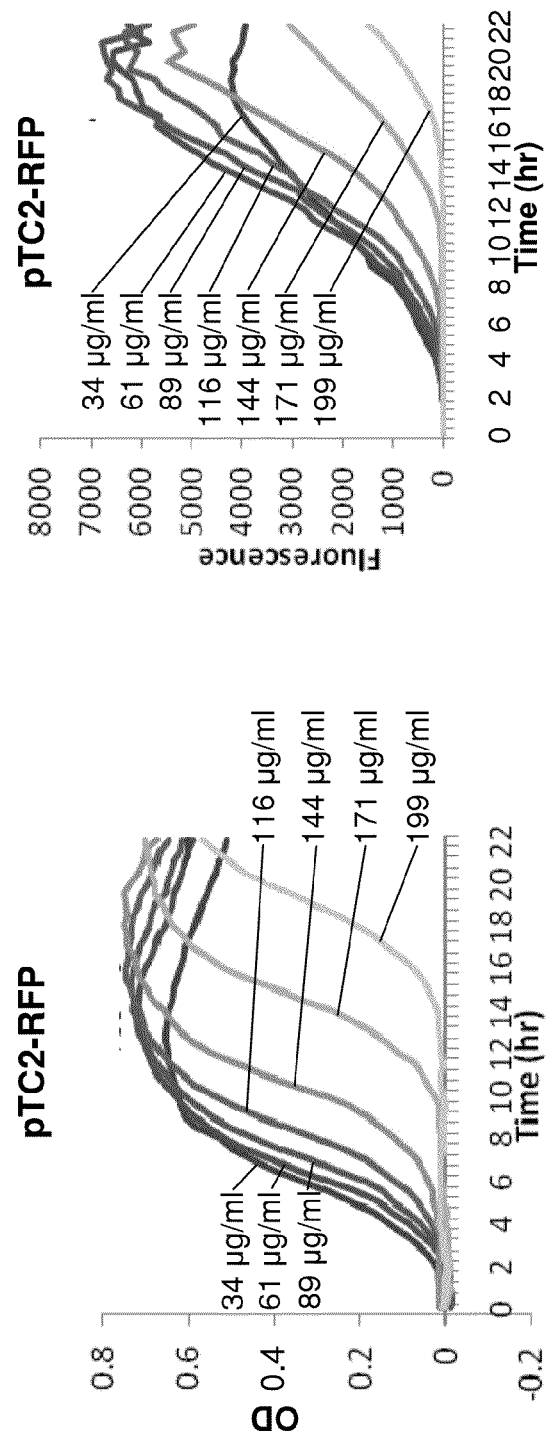
FIGS. 5A and 5B show growth and fluorescence curves, respectively, from *E. coli* cells transformed with the pTC2-RFP plasmid (see Tables 1 and 2) and grown in the presence of the shown concentrations (μg/ml) of chloramphenicol.

Cells transformed with pTC1-RFP, i.e., the full RFP coding sequence, showed strong growth (FIG. 3A) and strong RFP fluorescence (FIG. 3B) at all chloramphenicol concentrations. This indicated that both the RFP target protein and the chloramphenicol resistance marker were fully translated. Analysis by SDS-PAGE showed presence of the RFP protein product at the correct molecular weight (FIG. 3C), verifying full translation of the RFP protein. By contrast, cells transformed with pTC1-RFP*, i.e., the RFP coding sequence with the premature stop codon, showed essentially no growth (FIG. 4A) and no fluorescence (FIG. 4B).

These experiments show that expression of the response gene in the current expression system is coupled to full expression of the target gene and can be used to select for transformed cells that translate the target gene in its entirety.

A second set of experiments was carried out with the TC2 translation-coupling cassette with the same two RFP inserts as described above. The TC2 translation-coupling cassette had a different hairpin-forming sequence than that of TC1 (compare FIGS. 2A and 2B). Plasmid pTC2-RFP included the TC2 translation-coupling cassette with the full-length RFP coding sequence, and plasmid pTC2-RFP* included the TC2 cassette with the truncated RFP coding sequence. In cells harboring pTC2-RFP, both growth (FIG. 5A) and fluorescence (FIG. 5B) trended inversely with increasing chloramphenicol concentration. By contrast, cells harboring pTC2-RFP* showed no growth (FIG. 6A) or detectable fluorescence (FIG. 6B). These results indicated that translation of the response gene ($Cm^R$) was coupled to the translation of the target gene (RFP).

As with the first set of experiments, these data show that expression of the response gene in the current expression system is coupled to full translation of the target gene and can be used to select for transformed cells that translate the target gene in its entirety.

A third set of proof-of-concept experiments was performed with the TC4 translation-coupling cassette. The TC4 translation-coupling cassette included the same secondary structure-forming sequence as TC2 but contained a kanamycin-resistance marker in place of a chloramphenicol marker (see FIGS. 2B and 2D and Table 1). The same two RFP genes used in the previous set of experiments were cloned into the target-gene cloning site to generate pTC4-RFP and pTC4-RFP* (Table 2). E. coli cells transformed with either pTC4-RFP and pTC4-RFP* were cultured in the presence of 0, 12.5, 25, 50, 100, and 200 µg/ml kanamycin. Both growth (FIG. 7A) and fluorescence (FIG. 7B) of cells harboring pTC4-RFP trended inversely with increasing kanamycin concentration. By contrast, cells harboring pTC4-RFP* displayed no growth in the presence of kanamycin (FIG. 8A) and no detectable fluorescence (FIG. 8B).

These data again show that expression of the response gene in the current expression system is coupled to full translation of the target gene and can be used to select for transformed cells that translate the target gene in its entirety. Further, these experiments show that the system can be used with any of several different response genes.

In a fourth set of experiments, the translation-coupling system was used to assess expression of a previously uncharacterized gene ("Gene X") in E. coli. Gene X encodes a protein comprising eight predicted domains (FIG. 9) and, at about 9 kb, is much larger than usual E. coli genes.

To test expression of Gene X in E. coli, the full-length gene was cloned into the target-gene cloning site of the TC4 translation-coupling cassette, and the latter was inserted into a plasmid to generate pTC4-D1-D8 (Table 2). The pTC4-D1-D8 plasmid was used to transform E. coli and the transformed cells were cultured in the presence of 50, 100, 150, 200, 250, and 300 µg/ml kanamycin. The cells failed to grow at all concentrations of kanamycin (FIG. 10), indicating that the full-length gene did not successfully express.

In light of the failed growth of the full-length gene, smaller (1-3 kb) sections of Gene X based on the domain architecture of the protein were used as target genes and tested for expression using the same protocol as for the full-length gene. A gene fragment encoding roughly the N-terminal third of the protein (Domains 1-2) was used to generate pTC4-D1-D2 (Table 2). Cells harboring this plasmid successfully translated the D1-D2 polypeptide, as evidenced by growth in kanamycin (FIG. 11A) and SDS-PAGE analysis of the His-tagged, Ni-NTA-purified protein fragment (FIG. 11B). Similarly, a gene fragment encoding roughly the central third of the full-length protein (Domains 3-5) was used to generate pTC4-D3-D5. This fragment also successfully translated (FIGS. 12A and 12B). A gene fragment encoding roughly the C-terminal third of the protein (Domains 6-8) was used to generate pTC4-D6-D8 (Table 2). Cells harboring this plasmid did not successfully translate the fragment, as evidenced by a lack of growth in kanamycin (FIG. 13A; the curve at 300 µg/ml kanamycin appears to be a contaminant) and lack of a detectable band with SDS-PAGE (FIG. 13B). Future experiments will use error-prone PCR to generate D6-D8 fragments for use as target genes in the present system to identify mutant genes that can be efficiently expressed.

This series of experiments shows that the translation-coupling cassettes disclosed herein can be used to assess expression levels of a previously unknown, uncharacterized, and unexpressed target gene by selecting or screening for activity of the response gene. This system is amenable for use in a high-throughput system and real-time detection of target-gene expression.

Future experiments will study the relationship between expression level of the target gene and resistance generated by expression of the antibiotic resistance marker. This will be performed by using translation start sequences of varying efficiency (predicted by Salis et al. *Nature Biotechnology* (2009) 27:946-950) for RFP as a target gene, and monitoring both RFP fluorescence and RFP abundance by Western blot. We predict that levels of antibiotic resistance will correlate with levels of fluorescence and RFP abundance.

We claim:

1. A translation-coupling cassette comprising:
a target gene or a target-gene cloning site configured for forming the target gene;
a response gene or a response-gene cloning site configured for inserting a response gene therein;
a response-gene translation control element that, in a transcript of the translation-coupling cassette, controls translation of the response gene or a response gene inserted in the response gene cloning site; and
a secondary structure-forming sequence that, in the transcript of the translation-coupling cassette, reversibly forms a secondary structure that masks the response-gene translation control element and encompasses at least a portion of the 3' end of the coding sequence of the target gene, wherein at least part of the secondary structure-forming sequence is translationally linked with the target-gene cloning site or the target gene.

2. The translation-coupling cassette of claim 1 wherein the target-gene cloning site or the response-gene cloning site includes a multiple cloning site.

3. The translation-coupling cassette of claim 1 wherein the target-gene cloning site or the response-gene cloning site includes a ligation-independent cloning site.

4. The translation-coupling cassette of claim 1 further comprising a protein tag-encoding sequence, wherein the protein tag-encoding sequence forms or is configured to form part of the 3' end of the target gene coding sequence.

5. The translation-coupling cassette of claim 1 wherein the response gene is a screenable gene.

6. The translation-coupling cassette of claim 1 wherein the response gene is a selectable gene.

7. The translation-coupling cassette of claim 1 wherein the response-gene translation control element is a ribosome binding site.

8. The translation-coupling cassette of claim 7 wherein the ribosome binding site comprises a Shine-Dalgarno sequence or derivative thereof.

9. The translation-coupling cassette of claim 7 wherein the ribosome binding site comprises an AT-rich sequence.

10. The translation-coupling cassette of claim 1 further comprising a linker disposed between the response-gene translation control element and the response gene or the response-gene cloning site.

11. The translation-coupling cassette of claim 1 wherein the secondary structure formed by the secondary structure-forming sequence in the transcript includes a stem loop.

12. The translation-coupling cassette of claim 1 wherein the secondary structure-forming sequence at least partially includes the response-gene translation control element.

13. The translation-coupling cassette of claim 12 wherein the secondary structure-forming sequence further includes a stop codon, the stop codon being translationally linked with the target-gene cloning site or translationally linked in-frame with the target gene.

14. The translation-coupling cassette of claim 13 wherein the secondary structure-forming sequence at least partially includes a protein tag-encoding sequence, wherein the protein tag-encoding sequence forms or is configured to form part of the 3' end of the target gene coding sequence.

15. The translation-coupling cassette of claim 1 wherein the secondary structure-forming sequence is selected from the group consisting of bases 18-46 of SEQ ID NO:1, bases 26-60 of SEQ ID NO:2, bases 26-60 of SEQ ID NO:3, bases 26-60 of SEQ ID NO:4, and bases 5-51 of SEQ ID NO:5.

16. The translation-coupling cassette of claim 1 wherein the translation-coupling cassette is included within a vector capable of being introduced in a host.

17. The translation-coupling cassette of claim 1 further including a host comprising the translation-coupling cassette.

18. The translation-coupling cassette claim 17 wherein the host is a prokaryote.

19. The translation-coupling cassette of claim 1 wherein the secondary structure-forming sequence consists of sequence that forms secondary structure in the transcript of the translation-coupling cassette.

20. The translation-coupling cassette of claim 1 wherein the secondary structure-forming sequence comprises a base that, in the transcript of the translation-coupling cassette, base pairs directly with at least a portion of the response-gene translation control element, wherein the base is translationally linked with the target-gene cloning site or the target gene.

21. The translation-coupling cassette of claim 1 wherein the response-gene translation control element is translationally linked with the target-gene cloning site or the target gene.

* * * * *